(12) United States Patent
Rivas

(10) Patent No.: US 10,371,667 B2
(45) Date of Patent: Aug. 6, 2019

(54) BAW SENSOR WITH PASSIVE MIXING STRUCTURES

(71) Applicant: Qorvo US, Inc., Greensboro, NC (US)

(72) Inventor: Rio Rivas, Bend, OR (US)

(73) Assignee: QORVO US, INC., Greensboro, NC (US)

(*) Notice: Subject to any disclaimer, the term of this patent is extended or adjusted under 35 U.S.C. 154(b) by 433 days.

(21) Appl. No.: 15/353,060

(22) Filed: Nov. 16, 2016

(65) Prior Publication Data

US 2017/0138935 A1    May 18, 2017

Related U.S. Application Data

(60) Provisional application No. 62/255,625, filed on Nov. 16, 2015.

(51) Int. Cl.
*H01L 41/107* (2006.01)
*G01N 29/22* (2006.01)
(Continued)

(52) U.S. Cl.
CPC ........... *G01N 29/222* (2013.01); *B01F 5/061* (2013.01); *B01F 11/025* (2013.01); *B01F 13/0059* (2013.01); *B01L 3/502707* (2013.01); *B01L 3/502715* (2013.01); *B33Y 10/00* (2014.12); *B33Y 80/00* (2014.12); *G01N 29/022* (2013.01); *B01F 2005/0636* (2013.01); *B01L 2300/0636* (2013.01); *B01L 2300/0645* (2013.01); *B01L 2300/0819* (2013.01);
(Continued)

(58) Field of Classification Search
CPC .......... B01F 2005/0635; B01F 13/0059; B01L 2300/0636; B01L 2300/0645; B01L 2300/0819; B01L 2400/086; G01N 29/222; G01N 29/022; G01N 2291/014; G01N 2291/0255; G01N 2291/0256; G01N 2291/0426; B33Y 80/00; B33Y 10/00
USPC .......................................... 310/311–371, 800
See application file for complete search history.

(56) References Cited

U.S. PATENT DOCUMENTS

| 4,640,756 A | 2/1987 | Wang et al. |
| 7,468,608 B2 | 12/2008 | Feucht et al. |

(Continued)

OTHER PUBLICATIONS

Miller, "The Stokes-Einstein Law for Diffusion in Solution," *Proceedings of the Royal Society of London. Series A, Containing Papers of a Mathematical and Physical Character* (1905-1934), Jan. 1924, 106(70):724-49.

(Continued)

*Primary Examiner* — Thomas Dougherty
(74) *Attorney, Agent, or Firm* — Mueting, Raasch & Gebhardt, P.A.

(57) ABSTRACT

A fluidic device includes a base structure, a wall structure, and a cover structure bounding a fluidic passage containing a functionalized active region of at least one bulk acoustic wave (BAW) resonator structure. One or more of the wall structure, the cover structure, or a portion of the base structure includes multiple features (e.g., protrusions and/or recesses) configured to interact with fluid flowing within the fluidic passage to promote mixing between constituents of the fluid. Methods for fabricating a fluidic device, as well as methods for biological or chemical sensing using a fluidic device, are further provided.

20 Claims, 13 Drawing Sheets

(51) Int. Cl.
　　　　*B33Y 10/00*　　　　(2015.01)
　　　　*B33Y 80/00*　　　　(2015.01)
　　　　*B01L 3/00*　　　　(2006.01)
　　　　*G01N 29/02*　　　　(2006.01)
　　　　*B01F 5/06*　　　　(2006.01)
　　　　*B01F 11/02*　　　　(2006.01)
　　　　*B01F 13/00*　　　　(2006.01)

(52) U.S. Cl.
　　　CPC . *B01L 2400/0436* (2013.01); *B01L 2400/086* (2013.01); *G01N 2291/014* (2013.01); *G01N 2291/0255* (2013.01); *G01N 2291/0256* (2013.01); *G01N 2291/0426* (2013.01)

(56) References Cited

U.S. PATENT DOCUMENTS

| | | | |
|---|---|---|---|
| 8,409,875 | B2 | 4/2013 | Johal et al. |
| 2015/0177045 | A1* | 6/2015 | Cobianu ............ G01F 23/2968 367/99 |
| 2017/0117871 | A1* | 4/2017 | Rivas .................... H03H 9/175 |
| 2017/0120242 | A1* | 5/2017 | Rivas .................... G01N 29/022 |
| 2017/0122911 | A1* | 5/2017 | McCarron ............ G01N 29/036 |
| 2017/0122912 | A1* | 5/2017 | Fattinger .............. G01N 29/022 |
| 2017/0122936 | A1* | 5/2017 | Rivas ................. G01N 33/5438 |
| 2017/0134001 | A1* | 5/2017 | Belsick ................. G01N 29/022 |
| 2017/0134002 | A1* | 5/2017 | Rivas ............... B01L 3/502707 |
| 2017/0149408 | A1* | 5/2017 | Belsick .................. H03H 9/175 |
| 2017/0168017 | A1* | 6/2017 | Rivas .................... G01N 29/022 |
| 2017/0168026 | A1* | 6/2017 | Morton ............. B01L 3/502715 |
| 2017/0227497 | A1* | 8/2017 | Rivas .................... G01N 29/022 |
| 2017/0261503 | A1* | 9/2017 | Murdock ............. G01N 29/022 |
| 2017/0294892 | A1* | 10/2017 | Diep .................... G01N 29/036 |
| 2018/0034438 | A1* | 2/2018 | Ryder .................. G01N 29/036 |
| 2018/0048280 | A1* | 2/2018 | Ryder .................. G01N 33/536 |

OTHER PUBLICATIONS

Qorvo US, Inc., "Summary of Sales Activity of Predecessor to Applicant Concerning Tilted C-Axis Aluminum Nitride Products," Unpublished, Jan. 10, 2017, 1 page.

Bjurström, J. et al., "Design and Fabrication of Temperature Compensated Liquid FBAR Sensors," IEEE Ultrasonics Symposium, Oct. 2-6, 2006, pp. 894-897.

Chen, Ying-Chung et al., "The Liquid Sensor Using Thin Film Bulk Acoustic Resonator with C-Axis Tilted AlN Films," Journal of Nanomaterials, vol. 2013, Article ID 245095, 2013, 8 pages.

Corso, Christopher et al., "Development of a Simple Inexpensive Bulk Acoustic Wave (BAW) Nanosensor for Cancer Biomarkers: Detection of Secreted Sonic Hedgehog from Prostate Cancer Cells," Abstract #8866, Winship Cancer Institute, Emory University, Georgia Institute of Technology, Oct. 2012, 1 page.

Groner, M. D. et al., "Gas diffusion barriers on polymers using $Al_2O_3$ atomic layer deposition," Applied Physics Letters, vol. 88, Jan. 31, 2006, pp. 051907-1 to 051907-3.

Lee, Chia-Yen et al., "Microfluidic Mixing: A Review," International Journal of Molecular Sciences, vol. 12, May 18, 2011, pp. 3263-3287.

Link, Mathias, "Study and realization of shear wave mode solidly mounted film bulk acoustic resonators (FBAR) made of c-axis inclined zinc oxide (ZnO) thin films: application as gravimetric sensors in liquid environments," Université Henri Poincaré—Nancy I, Thesis, Sep. 14, 2006, 225 pages.

Luo, J. K. et al., "Acoustic Wave Based Microfluidics and Lab-on-a-Chip," Modeling and Measurement Methods for Acoustic Waves and for Acoustic Microdevices, Chapter 21, Aug. 28, 2013, InTech, pp. 515-556.

Meyer, Jens et al., "$Al_2O_3/ZrO_2$ Nanolaminates as Ultrahigh Gas-Diffusion Barriers—A Strategy for Reliable Encapsulation of Organic Electronics," Advanced Materials, vol. 21, 2009, pp. 1845-1849.

Milyutin, Evgeny, "Theoretical and Experimental Study of Piezoelectric Modulated AlN Thin Films for Shear Mode BAW Resonators," EPFL, Thesis No. 5113, Nov. 4, 2011, 109 pages.

Munir, Farasat, "A Fast, Scalable Acoustic Resonator-Based Biosensor Array System for Simultaneous Detection of Multiple Biomarkers," Thesis, Georgia Institute of Technology, Dec. 2012, 160 pages.

Nguyen, Nam-Trung et al., "Micromixers—a review," Journal of Micromechanics and Microengineering, vol. 15, Dec. 8, 2004, pp. R1-R16.

Nirschl, Martin et al., "CMOS-Integrated Film Bulk Acoustic Resonators for Label-Free Biosensing," Sensors, vol. 10, No. 5, Apr. 27, 2010, pp. 4180-4193.

Stroock, Abraham D. et al., "Chaotic Mixer for Microchannels," Science, vol. 295, Jan. 25, 2002, pp. 647-651.

Suh, Yong Kweon et al., "A Review on Mixing in Microfluidics," Micromachines, vol. 1, No. 3, Sep. 30, 2010, pp. 82-111.

Yu, Hongyu et al., "Ultra Temperature-Stable Bulk-Acoustic-Wave Resonators with $SiO_2$ Compensation Layer," IEEE Transactions on Ultrasonics, Ferroelectrics, and Frequency Control, vol. 54, No. 10, Oct. 2007, pp. 2102-2109.

Zhou, Yan et al., "Interfacial Structures and Properties of Organic Materials for Biosensors: An Overview," Sensors, vol. 12, Nov. 6, 2012, pp. 15036-15062.

\* cited by examiner

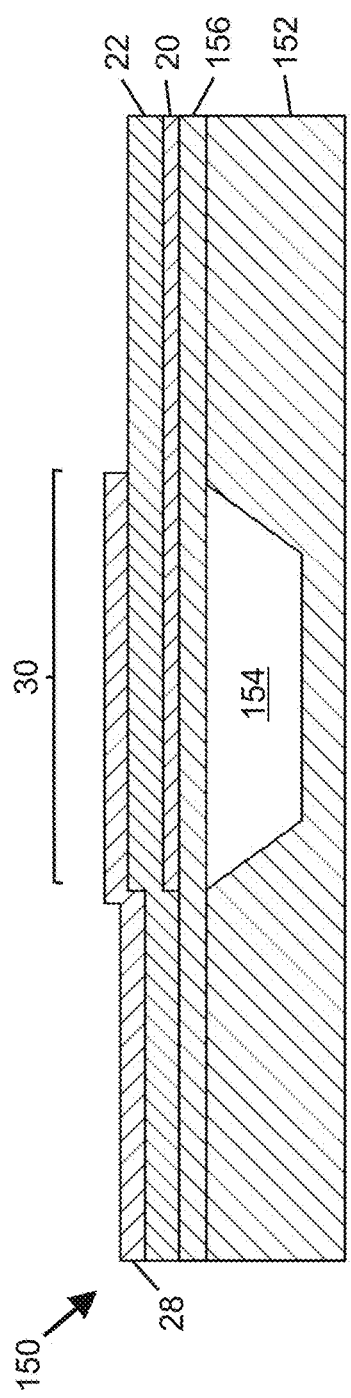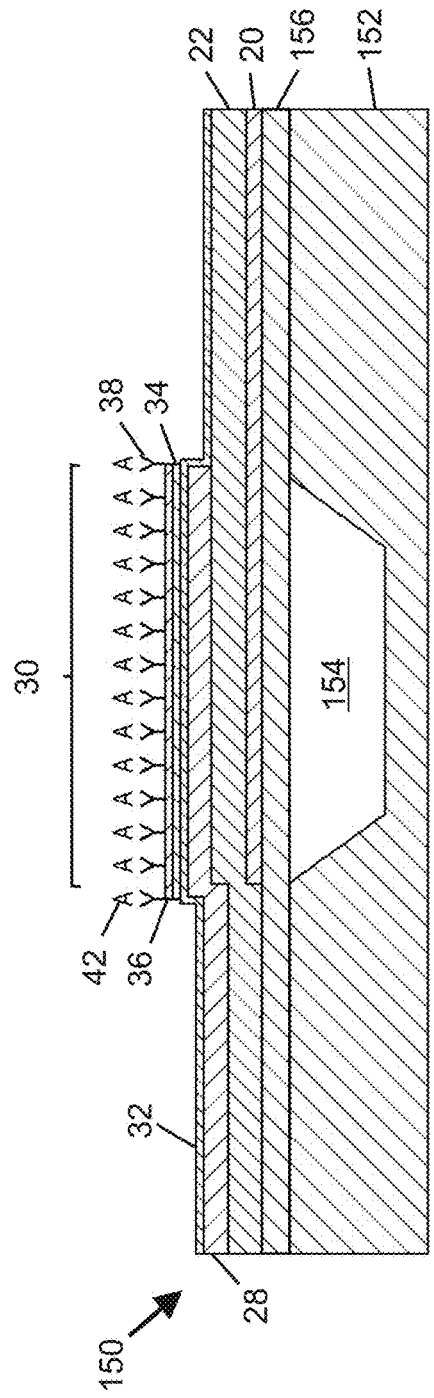

BAW SENSOR WITH PASSIVE MIXING STRUCTURES

STATEMENT OF RELATED APPLICATIONS

This application claims the benefit of provisional patent application Ser. No. 62/255,625, filed Nov. 16, 2015, the disclosure of which is hereby incorporated by reference herein in its entirety.

TECHNICAL FIELD

The present disclosure relates to fluidic devices incorporating acoustic resonators, including fluidic devices and related systems suitable for biosensing or biochemical sensing applications.

BACKGROUND

A biosensor (or biological sensor) is an analytical device including a biological element and a transducer that converts a biological response into an electrical signal. Certain biosensors involve a selective biochemical reaction between a specific binding material (e.g., an antibody, a receptor, a ligand, etc.) and a target species (e.g., molecule, protein, DNA, virus, bacteria, etc.), and the product of this highly specific reaction is converted into a measurable quantity by a transducer. Other sensors may utilize a non-specific binding material capable of binding multiple types or classes of molecules or other moieties that may be present in a sample, such as may be useful in chemical sensing applications. The term "functionalization material" may be used herein to generally relate to both specific and non-specific binding materials. Transduction methods may be based on various principles, such as electrochemical, optical, electrical, acoustic, and so on. Among these, acoustic transduction offers a number of potential advantages, such as being real time, label-free, and low cost, as well as exhibiting high sensitivity.

An acoustic wave device employs an acoustic wave that propagates through or on the surface of a piezoelectric material, whereby any changes to the characteristics of the propagation path affect the velocity and/or amplitude of the wave. Presence of functionalization material embodied in a specific binding material along an active region of an acoustic wave device permits a specific analyte to be bound to the specific binding material, thereby altering the mass being vibrated by the acoustic wave and altering the wave propagation characteristics (e.g., velocity, thereby altering resonance frequency). Changes in velocity can be monitored by measuring the frequency, amplitude-magnitude, or phase characteristics of the acoustic wave device, and can be correlated to a physical quantity being measured.

In the case of a piezoelectric crystal resonator, an acoustic wave may embody either a bulk acoustic wave (BAW) propagating through the interior of a piezoelectric material, or a surface acoustic wave (SAW) propagating on the surface of the piezoelectric material. SAW devices involve transduction of acoustic waves (commonly including two-dimensional Rayleigh waves) utilizing interdigital transducers along the surface of a piezoelectric material, with the waves being confined to a penetration depth of about one wavelength. BAW devices typically involve transduction of an acoustic wave using electrodes arranged on opposing top and bottom surfaces of a piezoelectric material. In a BAW device, three wave modes can propagate, namely, one longitudinal mode (embodying longitudinal waves, also called compressional/extensional waves), and two shear modes (embodying shear waves, also called transverse waves), with longitudinal and shear modes respectively identifying vibrations where particle motion is parallel to or perpendicular to the direction of wave propagation. The longitudinal mode is characterized by compression and elongation in the direction of the propagation, whereas the shear modes consist of motion perpendicular to the direction of propagation with no local change of volume. Longitudinal and shear modes propagate at different velocities. In practice, these modes are not necessarily pure modes, as the particle vibration, or polarization, is neither purely parallel nor purely perpendicular to the propagation direction. The propagation characteristics of the respective modes depend on the material properties and propagation direction respective to the crystal axis orientations. The ability to create shear displacements is beneficial for operation of acoustic wave devices with fluids (e.g., liquids) because shear waves do not impart significant energy into fluids.

Certain piezoelectric thin films are capable of exciting both longitudinal and shear mode resonance, such as hexagonal crystal structure piezoelectric materials including (but not limited to) aluminum nitride (AlN) and zinc oxide (ZnO). To excite a wave including a shear mode using a piezoelectric material arranged between electrodes, a polarization axis in a piezoelectric thin film must generally be non-perpendicular to (e.g., tilted relative to) the film plane. In biological sensing applications involving liquid media, the shear component of the resonator is used. In such applications, piezoelectric material may be grown with a c-axis orientation distribution that is non-perpendicular relative to a face of an underlying substrate to enable a BAW resonator structure to exhibit a dominant shear response upon application of an alternating current signal across electrodes thereof.

Typically, BAW devices are fabricated by micro-electromechanical systems (MEMS) fabrication techniques owing to the need to provide microscale features suitable for facilitating high frequency operation. In the context of biosensors, functionalization materials (e.g., specific binding materials; also known as bioactive probes or agents) may be deposited on sensor surfaces by microarray spotting (also known as microarray printing) using a microarray spotting needle. Functionalization materials providing non-specific binding utility (e.g., permitting binding of multiple types or species of molecules) may also be used in certain contexts, such as chemical sensing.

Under typical operating conditions, flows in microfluidic channels (also termed "microchannels", or "fluidic passages") are laminar. Fluids in laminar flow tend to follow parallel streamline paths, such that the chaotic fluctuations of velocity that tend to homogenize fluids in turbulent flows are absent. Multiple fluids introduced in a standard microfluidic channel generally will not mix with each other, except at a common interface between the fluids via diffusion, and the diffusion process is typically slow compared with the flow of fluid along a principal axis of a microfluidic channel. The same principles that inhibit rapid mixing of fluids flowing under laminar conditions in a microfluidic channel also affect the distribution of analytes contained in one or more fluids flowing within a microfluidic channel. Fick's first law of diffusion states that flux moves from regions of high concentration to regions of low concentration. Secondarily, the flux rate is proportional to the concentration gradient difference. In a volume of fluid containing an analyte and advancing in a horizontal direction through a microfluidic channel having functionalization material arranged along a bottom surface of the microfluidic channel, the fluid volume may be modeled as a moving "stack" of horizontal fluid layers. Even if it is assumed that analyte concentration is constant in each layer of the stack forming the fluid volume upon entering the microfluidic channel, following passage of the fluid volume over the functionalization material, a lowermost fluid layer of the stack will exhibit reduced or depleted analyte concentration due to binding of analyte with the functionalization material. But since diffusion is slow in a direction perpendicular to the direction of fluid flow through the microfluidic channel, and analyte needs to diffuse to a surface bearing functionalization material to bind, analyte present in fluid layers other than the lowermost fluid layer may not be available for binding with the functionalization material along the bottom surface of the microfluidic channel within a reasonable period of time.

Thus, conventional biochemical sensing devices may suffer from inconsistent distribution of target species in a sample and/or a low rate of analyte binding that may extend the time necessary to complete measurement of a particular sample. Accordingly, there is a need for fluidic devices incorporating BAW resonator structures, such as for biosensing or biochemical sensing applications, that overcome limitations associated with conventional devices.

SUMMARY

The present disclosure relates to a fluidic device including a base structure, a wall structure, and a cover structure bounding a fluidic passage containing a functionalized active region of at least one bulk acoustic wave (BAW) resonator structure formed by the base structure. The fluidic passage is configured to receive a fluid including multiple constituents. At least one of the wall structure, the cover structure, or a portion of the base structure includes multiple features (e.g., patterned features, such as multiple protrusions and/or recesses) configured to interact with fluid flowing within the fluidic passage to promote mixing between constituents of the fluid. Such mixing desirably serves to reduce stratification of analyte, increase binding of analyte with functionalization material, and reduce measurement time. Methods for fabricating such a fluidic device, as well as methods for biological or chemical sensing using such a fluidic device, are further provided.

In one aspect, a fluidic device includes: a base structure comprising: (i) a substrate; (ii) at least one bulk acoustic wave resonator structure supported by the substrate, the at least one bulk acoustic wave resonator structure including a piezoelectric material, a top side electrode arranged over a portion of the piezoelectric material, and a bottom side electrode arranged below at least a portion of the piezoelectric material, wherein a portion of the piezoelectric material is arranged between the top side electrode and the bottom side electrode to form an active region; and (iii) at least one functionalization material arranged over at least a portion of the active region; a wall structure arranged over at least a portion of the base structure and defining lateral boundaries of a fluidic passage containing the active region and being configured to receive a fluid comprising multiple constituents; and a cover structure arranged over the wall structure and defining an upper boundary of the fluidic passage. The base structure defines a lower boundary of the fluidic passage, and one or more of the wall structure, the cover structure, or a portion of the base structure non-coincident with the active region comprises a plurality of features configured to interact with fluid flowing within the fluidic passage to promote mixing between constituents of the fluid.

In certain embodiments, the plurality of features comprises a plurality of recesses or a plurality of protrusions. In certain embodiments, the plurality of features is defined in or on the wall structure. In certain embodiments, the plurality of features is defined in or on the cover structure. In certain embodiments, the plurality of features is defined in or on a portion of the base structure non-coincident with the active region.

In certain embodiments, the wall structure and the cover structure are embodied in a monolithic body structure. In certain embodiments, the wall structure and the base structure are embodied in a monolithic body structure.

In certain embodiments, the cover structure comprises a cover layer, the wall structure comprises at least one wall layer, and the at least one wall layer is arranged between the base structure and the cover layer. In certain embodiments, the at least one bulk acoustic wave resonator structure comprises a plurality of bulk acoustic wave resonator structures.

In certain embodiments (e.g., in which the at least one BAW resonator structure may be embodied in a solidly mounted resonator) the base structure further includes at least one acoustic reflector element arranged between the substrate and the at least one bulk acoustic wave resonator structure. In other embodiments (e.g., in which the at least one BAW resonator structure may be embodied in a film bulk acoustic wave resonator (FBAR) structure, the substrate defines a recess arranged below the active region.

In certain embodiments, the piezoelectric material comprises a c-axis having an orientation distribution that is predominantly non-parallel to normal of a face of the substrate.

In certain embodiments, the at least one functionalization material comprises a specific binding material. In certain embodiments, the at least one functionalization material comprises a non-specific binding material.

In certain embodiments, the fluidic device further includes a self-assembled monolayer arranged between the at least one functionalization material and the top side electrode. In certain embodiments, the fluidic device further includes an interface layer arranged between the self-assembled monolayer and the top side electrode. In certain embodiments, the fluidic device further includes a hermeticity layer arranged between the interface layer and the top side electrode.

In another aspect, a method for biological or chemical sensing includes: supplying a fluid containing an analyte into the fluidic passage of a fluidic device as disclosed herein (e.g., wherein one or more of the wall structure, the cover structure, or a portion of the base structure non-coincident with the active region comprises a plurality of features configured to interact with fluid flowing within the fluidic passage to promote mixing between constituents, as outlined above), wherein said supplying is configured to cause at least some of the analyte to bind to the at least one functionalization material; inducing a bulk acoustic wave in the active region; and sensing a change in at least one of an amplitude-magnitude property, a frequency property, or a phase property of the at least one bulk acoustic wave resonator structure to indicate at least one of presence or quantity of target species bound to the at least one functionalization material.

In another aspect, a method for fabricating a fluidic device includes: forming a base structure including at least one bulk acoustic wave resonator structure supported by a substrate, wherein the at least one bulk acoustic wave resonator structure includes a piezoelectric material, a top side electrode is arranged over a portion of the piezoelectric material, a bottom side electrode is arranged below at least a portion of the piezoelectric material, and a portion of the piezoelectric material is arranged between the top side electrode and the bottom side electrode to form an active region; forming a wall structure over at least a portion of the base structure and defining lateral boundaries of a fluidic passage containing the active region and being configured to receive a fluid comprising multiple constituents; forming a cover structure arranged over the wall structure and defining an upper boundary of the fluidic passage, wherein a lower boundary of the fluidic passage is defined by the base structure; and depositing at least one functionalization material over the active region. According to such a method, at least one of (i) formation of the base structure, (ii) formation of the wall structure, or (iii) formation of the cover structure comprises forming a plurality of features configured to interact with fluid flowing within the fluidic passage to promote mixing between constituents of the fluid, and the plurality of features comprises at least one of a plurality of recesses or a plurality of protrusions.

In certain embodiments, the forming of a plurality of features configured to interact with fluid flowing within the fluidic passage comprises removing material of one or more of the wall structure, the cover structure, or the base structure via a subtractive material removal process. In certain embodiments, the forming of a plurality of features configured to interact with fluid flowing within the fluidic passage comprises adding material to one or more of the wall structure, the cover structure, or the base structure via an additive manufacturing process.

In another aspect, any of the foregoing aspects, and/or various separate aspects and features as described herein, may be combined for additional advantage. Any of the various features and elements as disclosed herein may be combined with one or more other disclosed features and elements unless indicated to the contrary herein.

Those skilled in the art will appreciate the scope of the present disclosure and realize additional aspects thereof after reading the following detailed description of the preferred embodiments in association with the accompanying drawing figures.

BRIEF DESCRIPTION OF THE DRAWINGS

The accompanying drawing figures incorporated in and forming a part of this specification illustrate several aspects of the disclosure, and together with the description serve to explain the principles of the disclosure.

FIG. 13A is a schematic cross-sectional view of a film bulk acoustic wave resonator (FBAR) structure usable in devices according to certain embodiments, with the FBAR structure including an inclined c-axis hexagonal crystal structure piezoelectric material, a substrate defining a cavity optionally covered by a support layer, and an active region registered with the cavity, with a portion of the piezoelectric material arranged between overlapping portions of a top side electrode and a bottom side electrode.

FIG. 13B is a schematic cross-sectional view of the FBAR structure according to FIG. 13A, following addition of a hermeticity layer, an interface layer, a self-assembled monolayer, and a functionalization (e.g., specific binding) material over at least portions of the FBAR structure.

DETAILED DESCRIPTION

Figure 1:
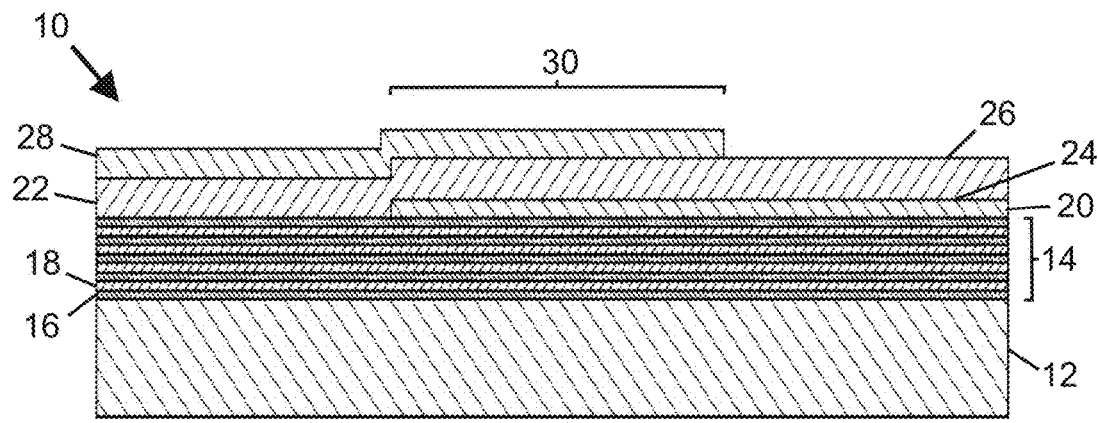
FIG. 1 is a schematic cross-sectional view of a portion of a bulk acoustic wave (BAW) MEMS resonator device usable with embodiments disclosed herein, including an active region with a piezoelectric material arranged between overlapping portions of a top side electrode and a bottom side electrode.

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

It should be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

It should also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

It should be understood that, although the terms "upper," "lower," "bottom," "intermediate," "middle," "top," and the like may be used herein to describe various elements, these elements should not be limited by these terms. These terms are only used to distinguish one element from another. For example, a first element could be termed an "upper" element and, similarly, a second element could be termed an "upper" element depending on the relative orientations of these elements, without departing from the scope of the present disclosure.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having meanings that are consistent with their meanings in the context of this specification and the relevant art and will not be interpreted in an idealized or overly formal sense unless expressly so defined herein.

The present disclosure relates to a fluidic device including a base structure, a wall structure, and a cover structure bounding a fluidic passage containing a functionalized active region of at least one bulk acoustic wave (BAW) resonator structure formed by the base structure. The fluidic passage is configured to receive a fluid including multiple constituents. At least one of the wall structure, the cover structure, or a portion of the base structure includes multiple features (e.g., patterned features, such as multiple protrusions and/or recesses) configured to interact with fluid flowing within the fluidic passage to promote mixing between constituents of the fluid. Such mixing desirably serves to reduce stratification of analyte, increase binding of analyte with functionalization material, and reduce measurement time. In certain embodiments, multiple protrusions and/or recesses may be provided on a textured surface having a repeating textural pattern. Methods for fabricating a fluidic device as disclosed herein, as well as methods for biological or chemical sensing using such a fluidic device, are further provided.

In certain embodiments, a BAW resonator structure comprises a hexagonal crystal structure piezoelectric material (e.g., aluminum nitride or zinc oxide) that includes a c-axis having an orientation distribution that is non-parallel (and also non-perpendicular) to normal of a face of a substrate over which the piezoelectric material is formed, thereby providing a quasi-shear mode acoustic resonator. Such a c-axis orientation distribution enables creation of shear displacements at certain frequencies (which beneficially enables operation of a BAW resonator-based sensing device in liquid environments), and enables creation of longitudinal displacements at other frequencies (which may be useful to promote localized mixing). Methods for forming hexagonal crystal structure piezoelectric materials including a c-axis having an orientation distribution that is predominantly non-parallel to normal of a face of a substrate are disclosed in U.S. patent application Ser. No. 15/293,063 filed on Oct. 13, 2016, with the foregoing application hereby being incorporated by reference herein. Additional methods for forming piezoelectric material having an inclined c-axis orientation are disclosed in U.S. Pat. No. 4,640,756 issued on Feb. 3, 1987, with the foregoing patent hereby being incorporated by reference herein.

Before describing fluidic devices with inlet ports orthogonal to functionalized active regions, exemplary bulk acoustic wave MEMS resonator devices, associated layers useful for providing biochemical sensing utility, and fluidic devices incorporating MEMS resonator devices will be introduced.

Micro-electrical-mechanical system (MEMS) resonator devices according to certain embodiments include a substrate, a BAW resonator structure arranged over at least a portion of the substrate, and a functionalization material arranged over at least a portion of an active region of the BAW resonator structure. Various layers may be arranged between the functionalization material and a top side electrode (which is coincident with the active region of the BAW resonator structure), such as: a hermeticity layer (e.g., to protect a top side electrode from corrosion in a liquid environment), an interface layer, and/or a self-assembled monolayer (SAM), with the interface layer and/or the SAM being useful to facilitate attachment of at least one overlying material layer, ultimately including functionalization material. In certain embodiments, the interface layer facilitates attachment of an overlying SAM, and the SAM facilitates attachment of an overlying functionalization material. In certain embodiments, multiple functionalization materials may be provided.

FIG. 1 is a schematic cross-sectional view of a portion of a bulk acoustic wave (BAW) MEMS resonator device 10 useable with embodiments disclosed herein. The resonator device 10 includes a substrate 12 (e.g., typically silicon or another semiconductor material), an acoustic reflector 14 arranged over the substrate 12, a piezoelectric material 22, and bottom and top side electrodes 20, 28. The bottom side electrode 20 is arranged along a portion of a lower surface 24 of the piezoelectric material 22 (between the acoustic reflector 14 and the piezoelectric material 22), and the top side electrode 28 is arranged along a portion of an upper surface 26 of the piezoelectric material 22. An area in which the piezoelectric material 22 is arranged between overlapping portions of the top side electrode 28 and the bottom side electrode 20 is considered an active region 30 of the resonator device 10. The acoustic reflector 14 serves to reflect acoustic waves and therefore reduce or avoid their dissipation in the substrate 12. In certain embodiments, the acoustic reflector 14 includes alternating thin layers 16, 18 of materials (e.g., silicon oxicarbide [SiOC], silicon nitride [$Si_3N_4$], silicon dioxide [$SiO_2$], aluminum nitride [AlN], tungsten [W], and molybdenum [Mo]) having different acoustic impedance values, optionally embodied in a quarter-wave Bragg mirror, deposited over the substrate 12. In certain embodiments, other types of acoustic reflectors may be used. Steps for forming the resonator device 10 may include depositing the acoustic reflector 14 over the substrate 12, followed by deposition of the bottom side electrode 20, followed by growth (e.g., via sputtering or other appropriate methods) of the piezoelectric material 22, followed by deposition of the top side electrode 28.

In certain embodiments, the piezoelectric material 22 comprises a hexagonal crystal structure piezoelectric material (e.g., aluminum nitride or zinc oxide) that includes a c-axis having an orientation distribution that is predominantly non-parallel to (and may also be non-perpendicular to) normal of a face of the substrate 12. Under appropriate conditions, presence of a c-axis having an orientation distribution that is predominantly non-parallel to normal of a face of a substrate enables a BAW resonator structure to be configured to exhibit a dominant shear response upon application of an alternating current signal across a top side electrode and a bottom side electrode.

The bulk acoustic wave MEMS resonator device 10 shown in FIG. 1 lacks any layers (e.g., including functionalization material) overlying the active region 30 that would permit the resonator device 10 to be used as a biochemical sensor. If desired, at least portions of the resonator device 10 shown in FIG. 1 (e.g., including the active region 30) may be overlaid with various layers, such as one or more of: a hermeticity layer, an interface layer, a self-assembled monolayer (SAM), and/or a functionalization material (which may include specific binding material or non-specific binding material).

Figure 2:
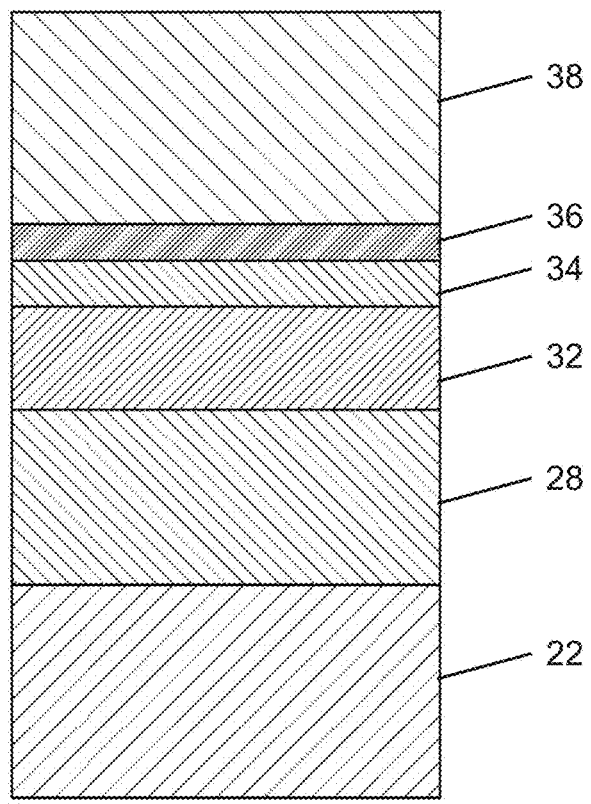
FIG. 2 is a schematic cross-sectional view of an upper portion of a BAW MEMS resonator device including a piezoelectric material and a top side electrode overlaid with a hermeticity layer, an interface layer, a self-assembled monolayer, and a functionalization (e.g., specific binding) material.

FIG. 2 is a schematic cross-sectional view of an upper portion of a BAW MEMS resonator device including a piezoelectric material 22 and a top side electrode 28 overlaid with a hermeticity layer 32, an interface layer 34, a self-assembled monolayer (SAM) 36, and a functionalization (e.g., specific binding) material 38. In certain embodiments, one or more blocking materials (not shown) may be applied during fabrication, such as over portions of the interface layer 34 to prevent localized attachment of one or more subsequently deposited layers, or (if applied over selected regions of the SAM 36 or functionalization material 38) to prevent analyte capture in regions not overlying the active region 30 of the BAW MEMS resonator device.

In certain embodiments, photolithography may be used to promote patterning of interface material or blocking material over portions of a MEMS resonator device. Photolithography involves use of light to transfer a geometric pattern from a photomask to a light-sensitive chemical photoresist on a substrate and is a process well known to those of ordinary skill in the semiconductor fabrication art. Typical steps employed in photolithography include wafer cleaning, photoresist application (involving either positive or negative photoresist), mask alignment, and exposure and development. After features are defined in photoresist on a desired surface, an interface layer may be patterned by etching in one or more gaps in a photoresist layer, and the photoresist layer may be subsequently removed (e.g., by using a liquid photoresist stripper, by ashing via application of an oxygen-containing plasma, or another removal process).

In certain embodiments, an interface layer (e.g., arrangeable between a top side electrode and a SAM) includes a hydroxylated oxide surface suitable for formation of an organosilane SAM. A preferred interface layer material including a hydroxylated oxide surface is silicon dioxide [$SiO_2$]. Alternative materials incorporating hydroxylated oxide surfaces for forming interface layers include titanium dioxide [$TiO_2$], tantalum pentoxide [$Ta_2O_5$], hafnium oxide [$HfO_2$], or aluminum oxide [$Al_2O_3$]. Other alternative materials incorporating hydroxylated oxide surfaces will be known to those skilled in the art, and these alternatives are considered to be within the scope of the present disclosure.

In other embodiments, an interface layer (e.g., arrangeable between a top side electrode and a SAM), or at least one electrode that is devoid of an overlying interface layer, includes gold or another noble metal (e.g., ruthenium, rhodium, palladium, osmium, iridium, platinum, or silver) suitable for receiving a thiol-based SAM that may be overlaid with functionalization material.

In certain embodiments incorporating electrode materials subject to corrosion, a hermeticity layer may be applied between a top side electrode and an interface layer. A hermeticity layer may be unnecessary when noble metals (e.g., gold, platinum, etc.) are used for top side electrodes. If provided, a hermeticity layer preferably includes a dielectric material with a low water vapor transmission rate (e.g., no greater than 0.1 g/m$^2$/day). Following deposition of a hermeticity layer and an interface layer, a SAM may be formed over the interface layer, with the SAM including an organosilane material in certain embodiments. The hermeticity layer protects a reactive electrode material (e.g., aluminum or aluminum alloy) from attack in corrosive liquid environments, and the interface layer facilitates proper chemical binding of the SAM.

In certain embodiments, a hermeticity layer and/or an interface layer may be applied via one or more deposition processes such as atomic layer deposition (ALD), chemical vapor deposition (CVD), or physical vapor deposition (PVD). Of the foregoing processes, ALD is preferred for deposition of at least the hermeticity layer (and may also be preferable for deposition of the interface layer) due to its ability to provide excellent conformal coating with good step coverage over device features so as to provide layer structures that are free of pinholes. Moreover, ALD is capable of forming uniformly thin layers that provide relatively little damping of acoustic vibrations that would otherwise result in degraded device performance. Adequacy of coverage is important for a hermeticity layer (if present) to avoid corrosion of the underlying electrode. If ALD is used for deposition of a hermeticity layer, then in certain embodiments a hermeticity layer may include a thickness in a range of from about 10 nm to about 25 nm. In certain embodiments, hermeticity layer thickness is about 15 nm, or from about 12 nm to about 18 nm. Conversely, if another process such as chemical vapor deposition is used, then a hermeticity layer may include a thickness in a range of from about 80 nm to about 150 nm or more, or in a range of from about 80 nm to about 120 nm. Considering both of the foregoing processes, hermeticity layer thicknesses may range from about 5 nm to about 150 nm. If ALD is used for deposition of an interface layer, then an interface layer may include a thickness in a range of from about 5 nm to about 15 nm. In certain embodiments, an interface layer may include a thickness of about 10 nm, or in a range of from about 8 nm to about 12 nm. Other interface layer thickness ranges and/or deposition techniques other than ALD may be used in certain embodiments. In certain embodiments, a hermeticity layer and an interface layer may be sequentially applied in a vacuum environment, thereby promoting a high-quality interface between the two layers.

If provided, a hermeticity layer may include an oxide, a nitride, or an oxynitride material serving as a dielectric material and having a low water vapor transmission rate (e.g., no greater than 0.1 g/m$^2$/day) according to certain embodiments. In certain embodiments, a hermeticity layer includes at least one of aluminum oxide [$Al_2O_3$] or silicon nitride [SiN]. In certain embodiments, an interface layer includes at least one of $SiO_2$, $TiO_2$, or $Ta_2O_5$. In certain embodiments, multiple materials may be combined in a single hermeticity layer, and/or a hermeticity layer may include multiple sublayers of different materials. Preferably, a hermeticity layer is further selected to promote compatibility with an underlying reactive metal (e.g., aluminum or aluminum alloy) electrode structure of an acoustic resonator structure. Although aluminum or aluminum alloys are frequently used as electrode materials in BAW resonator structures, various transition and post-transition metals can be used for such electrodes.

Following deposition of an interface layer (optionally arranged over an underlying hermeticity layer), a SAM is preferably formed over the interface layer. SAMs are typically formed by exposure of a solid surface to amphiphilic molecules with chemical groups that exhibit strong affinities for the solid surface. When an interface layer comprising a hydroxylated oxide surface is used, then organosilane SAMs are particularly preferred for attachment to the hydroxylated oxide surface. Organosilane SAMs promote surface bonding through silicon-oxygen (Si—O) bonds. More specifically, organosilane molecules include a hydrolytically sensitive group and an organic group and are therefore useful for coupling inorganic materials to organic polymers. An organosilane SAM may be formed by exposing a hydroxylated oxide surface to an organosilane material in the presence of trace amounts of water to form intermediate silanol groups. These groups then react with free hydroxyl groups on the hydroxylated oxide surface to covalently immobilize the organosilane. Examples of possible organosilane-based SAMs that are compatible with interface layers incorporating hydroxylated oxide surfaces include 3-glycidoxypropyltrimethoxysilane (GPTMS), 3-mercaptopropyltrimethoxysilane (MPTMS), 3-aminopropyltrimethoxysilane (APTMS), and octadecyltrimethoxysilane (OTMS), including their ethoxy- and chloro-variants. Additional silanes that may be used for SAMs include poly(ethylene glycol) (PEG) conjugated variants. Those skilled in the art will recognize that other alternatives exist, and these alternatives are considered to be within the scope of the present disclosure. An exemplary SAM may include a thickness in a range of at least 0.5 nm or more. Preferably, a SAM readily binds to the locally patterned interface layer but does not readily bind to other adjacent material layers (e.g., a hermeticity layer, a piezoelectric material, and/or a blocking material layer).

When an electrode and/or interface layer comprising gold or another noble metal is used, then thiol-based (e.g., alkanethiol-based) SAMs may be used. Alkanethiols are molecules with an S—H head group, a tail group, and a back bone comprising an alkyl chain. Thiols may be used on noble metal interface layers due to the strong affinity of sulfur for these metals. Examples of thiol-based SAMs that may be used include, but are not limited to, 1-dodecanethiol (DDT), 11-mercaptoundecanoic acid (MUA), and hydroxyl-terminated (hexaethylene glycol) undecanethiol (1-UDT). These thiols contain the same backbone, but different end groups—namely, methyl ($CH_3$), carboxyl (COOH), and hydroxyl-terminated hexaethylene glycol (HO—$(CH_2CH_2O)_6$) for DDT, MUA, and 1-UDT, respectively. In certain embodiments, SAMs may be formed by incubating gold surfaces in thiol solutions using a suitable solvent, such as anhydrous ethanol.

Following formation of a SAM, the SAM may be biologically functionalized, such as by receiving at least one functionalization (e.g., specific binding) material. In certain embodiments, specific binding materials may be applied on or over a SAM using a microarray spotting needle or other suitable methods. In certain embodiments, an interface layer may be patterned (e.g., using photolithographic masking and selective etching for defining the interface layer) with a high dimensional tolerance over only a portion of a BAW resonator structure (which includes a substrate), a SAM may be applied over the interface layer, and a subsequently applied specific binding material may be attached only to the SAM. In certain embodiments, patterning of an interface layer may provide a higher dimensional tolerance for positioning of the specific binding material than could be attained by microarray spotting alone. Examples of specific binding materials include, but are not limited to, antibodies, receptors, ligands, and the like. A specific binding material is preferably configured to receive a predefined target species (e.g., molecule, protein, DNA, virus, bacteria, etc.). A functionalization material including specific binding material may include a thickness in a range of from about 5 nm to about 1000 nm, or from about 5 nm to about 500 nm. In certain embodiments, an array of different specific binding materials may be provided over different active regions of a multi-resonator structure (i.e., one or more resonator structures including multiple active regions), optionally in combination with one or more active regions that are devoid of specific binding materials to serve as comparison (or "reference") regions. In certain embodiments, a functionalization (e.g., bio-functionalization) material may provide non-specific binding utility.

Certain embodiments are directed to a fluidic device including multiple bulk acoustic wave (BAW) MEMS resonator structures as disclosed herein and including a fluidic passage (e.g., a channel, a chamber, or the like) arranged to conduct a liquid to contact at least one functionalization (e.g., specific binding) material arranged over at least one active region of the BAW MEMS resonator structures. Such a device may be microfluidic in scale, and may comprise at least one microfluidic passage (e.g., having at least one dimension, such as height and/or width, of no greater than about 500 microns, or about 250 microns, or about 100 microns). For example, following fabrication of bulk acoustic wave MEMS resonator structures and deposition of a SAM over portions thereof (optionally preceded by deposition of a hermeticity layer and an interface layer), a microfluidic device may be fabricated by forming one or more walls defining lateral boundaries of a microfluidic passage over a first bulk acoustic wave MEMS resonator structure with an active region thereof arranged along a bottom surface of the microfluidic passage, and then enclosing the microfluidic passage using a cover or cap layer that may define fluidic ports (e.g., openings) enabling fluid communication with the microfluidic passage. In certain embodiments, functionalization (e.g., specific binding) material may be pre-applied to the active region of a bulk acoustic wave MEMS resonator structure before formation of the microfluidic passage; in other embodiments, functionalization material may be applied over an active region of a bulk acoustic wave resonator structure following formation of the microfluidic passage.

Walls of a microfluidic passage may be formed of any suitable material, such as laser-cut "stencil" layers of thin polymeric materials and/or laminates, optionally including one or more self-adhesive surfaces (e.g., adhesive tape). Optionally such walls may be formed prior to deposition of a SAM, functionalization material, and/or blocking layers, with an SU-8 negative epoxy resist or other photoresist material. In certain embodiments, a cover or cap layer may be integrally formed with one or more walls (e.g., via molding or another suitable process) to define a portion of an upper boundary as well as lateral boundaries of at least one fluidic passage, and the integrally formed partial cover/wall structure may be applied (e.g., adhered or otherwise bonded) over at least a portion of a bulk acoustic wave resonator structure to enclose the at least one fluidic passage.

In certain embodiments, a chemical or biological blocking material may be applied over a portion of a SAM to prevent attachment of a functionalization (e.g., specific binding) material over one or more selected regions of a BAW resonator structure (e.g., one or more regions apart from an active region). The proper choice of a chemical or biological blocking material (e.g., blocking buffer) for a given analysis depends on the type of target species or analyte present in a sample. Various types of blocking buffers such as highly purified proteins, serum, or milk may be used to block free sites on a SAM. Additional blockers include ethanolamine or polyethylene oxide (PEO)—containing materials. An ideal blocking buffer would bind to all potential sites of non-specific interaction away from an active region. To optimize a blocking buffer for a particular analysis, empirical testing may be used to determine signal-to-noise ratio. No single chemical or biological blocking material is ideal for every situation, since each antibody-antigen pair has unique characteristics.

Figure 3:
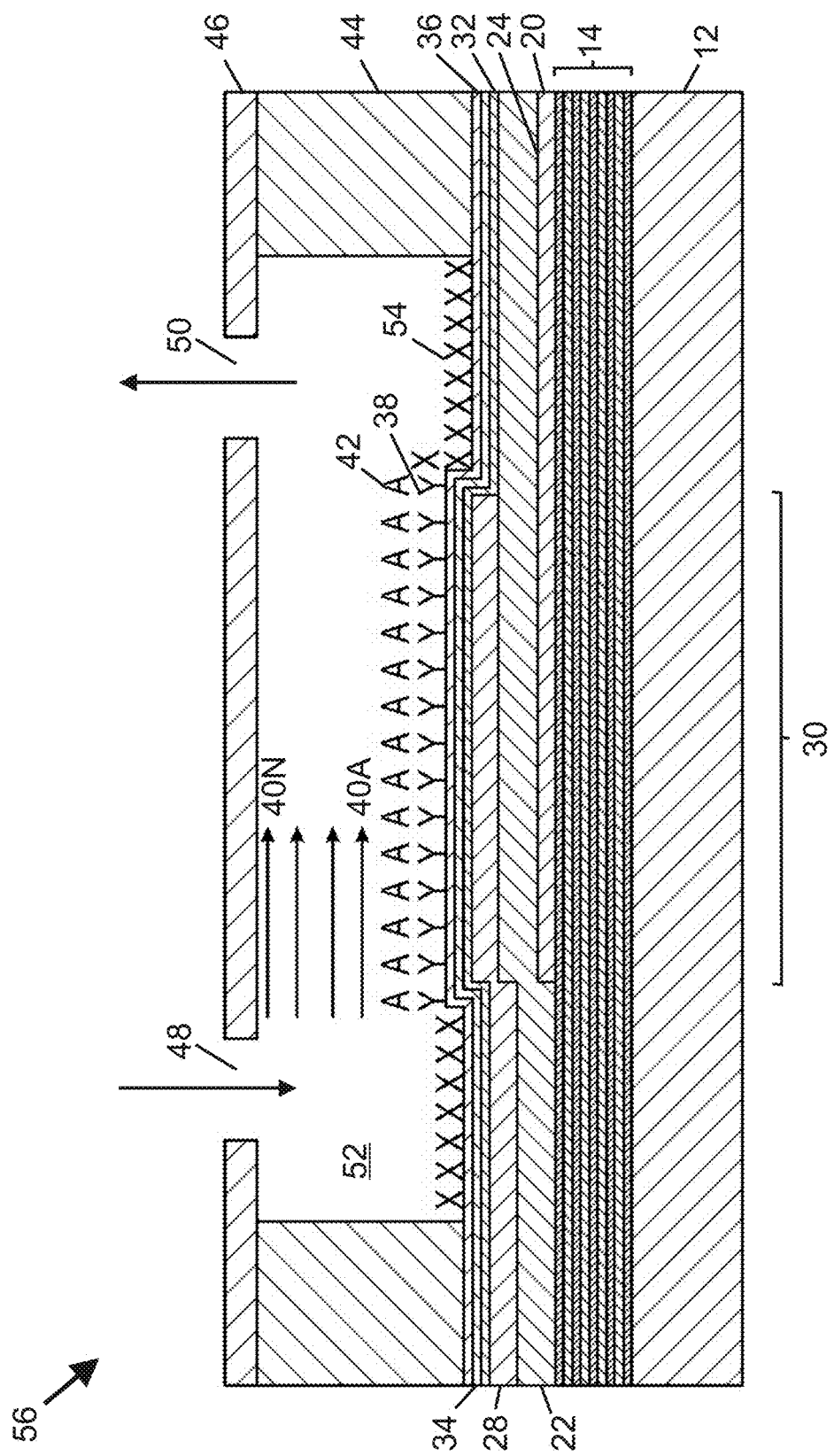
FIG. 3 is a schematic cross-sectional view of a portion of a fluidic device (e.g., a biochemical sensor device) including a fluidic passage bounded from below by a BAW resonator structure, bounded laterally by walls, and bounded from above by a cover or cap layer, with a self-assembled monolayer (SAM) arranged over the entire piezoelectric material and with a blocking material arranged over portions of the SAM non-coincident with an active region distal from fluidic ports defined in the cover or cap layer, to serve as a first comparison device intended to provide context for subsequently described embodiments of the disclosure.

FIG. 3 is a schematic cross-sectional view of a portion of a fluidic device 56 (e.g., a biochemical sensor device) including a fluidic passage 52 (which may be microfluidic in character) that is bounded from below by a bulk acoustic wave resonator structure including an active region 30, bounded laterally by a wall structure 44, and bounded from above by a cover or cap layer 46 defining a fluidic inlet port 48 and a fluidic outlet port 50, with the fluidic device 56 serving as a first comparison device intended to provide context for subsequently described embodiments of the disclosure. The fluidic device 56 includes a substrate 12 overlaid with an acoustic reflector 14, and a bottom side electrode 20 arranged generally below a piezoelectric material 22. A top side electrode 28 extends over a portion of the piezoelectric material 22, wherein a portion of the piezoelectric material 22 arranged between the top side electrode 28 and the bottom side electrode 20 embodies the active region 30 of the BAW resonator structure. The bottom side electrode 20 is arranged along a portion of a lower surface 24 of the piezoelectric material 22. The top side electrode 28 and the piezoelectric material 22 are overlaid with a hermeticity layer 32, an interface layer 34, and a self-assembled monolayer (SAM) 36. Portions of the SAM 36 between the active region 30 and the wall structure 44 are overlaid with a chemical or biological blocking material 54 to prevent localized attachment of functionalization material and/or analyte. A portion of the SAM 36 that is registered with the active region 30 is overlaid with a layer of functionalization (e.g., specific binding) material 38 arranged to bind at least one analyte. Walls of the wall structure 44 are laterally displaced from the active region 30 and extend upward from the SAM 36 to define lateral boundaries of the fluidic passage 52 containing the active region 30. The wall structure 44 may be formed of any suitable material, such as a laser-cut "stencil" layer of thin polymeric materials and/or laminate materials, optionally including one or more self-adhesive surfaces (e.g. adhesive tape). Optionally the wall structure 44 may be formed prior to deposition of the SAM 36, functionalization material 38, and chemical or biological blocking material 54 with an SU-8 negative epoxy resist or other photoresist material. The cover or cap layer 46 defining fluidic inlet and outlet ports 48, 50 is further provided to provide an upper boundary for the fluidic passage 52. The cover or cap layer 46 may be formed by defining fluidic inlet and outlet ports 48, 50 (e.g., via laser cutting or water jet cutting) in a layer of an appropriate material (e.g., a substantially inert polymer, glass, silicon, ceramic, or the like), and adhering the cover or cap layer 46 to top surfaces of the wall structure 44.

In use of the fluidic device 56, a fluid sample may be supplied through the fluidic inlet port 48 into the fluidic passage 52 over the active region 30 and then flow through the fluidic outlet port 50 to exit the fluidic passage 52. Due to the laminar nature of the fluid flow within the fluidic passage 52, the fluid volume may be modeled and behave as a "stack" of horizontal fluid layers including a lowermost fluid layer 40A and an uppermost fluid layer 40N. An analyte 42 contained in the lowermost fluid layer 40A of the fluid sample will tend to bind with functionalization material 38 arranged over the active region 30. Analyte contained in fluid layers above the lowermost fluid layer 40A (including the uppermost fluid layer 40N) may not be available to bind with the functionalization material 38, since diffusion of analyte (e.g., in a vertical direction) between the fluid layers 40A-40N may occur slowly. Assuming that sufficient analyte is present proximate to the lowermost fluid layer 40A to bind with functionalization material 38 arranged over the active region 30, when a bulk acoustic wave having a dominant shear component is induced in the active region 30 by supplying an electrical (e.g., alternating current) signal of a desired frequency to the bottom and top side electrodes 20, 28, a change in electroacoustic response (e.g., at least one of an amplitude-magnitude property, a frequency property, or a phase property, such as a shift in resonant frequency) of the BAW resonator structure may be detected to indicate a presence and/or quantity of analyte bound to the functionalization material 38.

Figure 4:
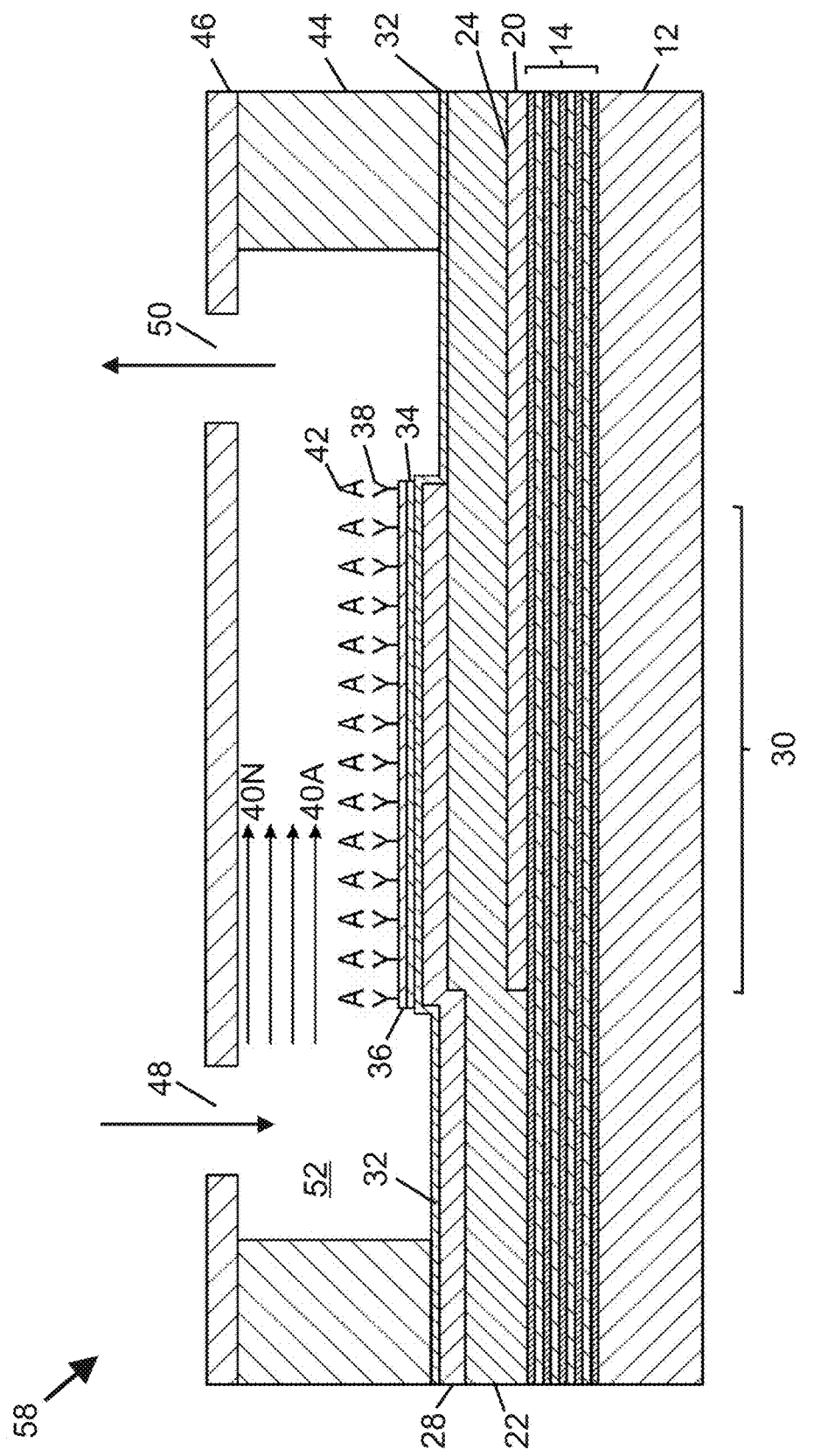
FIG. 4 is a schematic cross-sectional view of a portion of a fluidic device (e.g., a biochemical sensor device) including a fluidic passage bounded from below by a BAW resonator structure, bounded laterally by walls, and bounded from above by a cover or cap layer, with an interface layer, a SAM, and functionalization material arranged only over an active region distal from fluidic ports defined in the cover or cap layer, to serve as a second comparison device intended to provide context for subsequently described embodiments of the disclosure.

FIG. 4 is a schematic cross-sectional view of a portion of a fluidic device (e.g., a biochemical sensor device) 58 similar to the fluidic device 56 of FIG. 3, serving as a second comparison device intended to provide context for subsequently described embodiments of the disclosure. As compared to the fluidic device 56 of FIG. 3, the fluidic device 58 of FIG. 4 includes an interface layer 34 and a SAM 36 that are provided solely over an active region 30 instead of over an entirety of piezoelectric material 22. Such configuration may be provided by controlling lateral boundaries of the interface layer 34 (e.g., by photolithographic patterning and selective etching, for example). The fluidic device 58 includes a fluidic passage 52 that is bounded from below by a bulk acoustic wave resonator structure including the active region 30, bounded laterally by a wall structure 44, and bounded from above by a cover or cap layer 46 defining a fluidic inlet port 48 and a fluidic outlet port 50. The fluidic device 58 includes a substrate 12 overlaid with an acoustic reflector 14, and a bottom side electrode 20 arranged generally below the piezoelectric material 22. The bottom side electrode 20 is arranged along a portion of a lower surface 24 of the piezoelectric material 22. A top side electrode 28 extends over a portion of the piezoelectric material 22, wherein a portion of the piezoelectric material 22 arranged between the top side electrode 28 and the bottom side electrode 20 embodies the active region 30 of the BAW resonator structure. A hermeticity layer 32 is arranged over the top side electrode 28 and the piezoelectric material 22. The interface layer 34 and the SAM 36 are provided over a portion of the hermeticity layer 32 that is registered with the active region 30. The SAM 36 is overlaid with a layer of functionalization (e.g., specific binding) material 38 arranged to bind at least one analyte (e.g., analyte 42). Walls of the wall structure 44 are laterally displaced from the active region 30 and extend upward from the hermeticity layer 32 to define lateral boundaries of the fluidic passage 52 containing the active region 30. The cover or cap layer 46 defining the fluidic inlet port 48 and the fluidic outlet port 50 is provided over the wall structure 44 to provide an upper boundary for the fluidic passage 52. Operation of the fluidic device 58 of FIG. 4 is similar to the operation of the fluidic device 56 of FIG. 3. A volume of fluid may behave as a "stack" of horizontal fluid layers including a lowermost fluid layer 40A and an uppermost fluid layer 40N within the fluidic passage 52, wherein the lowermost fluid layer 40A is proximate to functionalization material 38 overlying the active region 30. Assuming the presence of sufficient analyte in the fluid (including the lowermost fluid layer 40A) when a bulk acoustic wave having a dominant shear component is induced in the active region 30 by supplying an electrical (e.g., alternating current) signal of a desired frequency to the bottom and top side electrodes 20, 28, then a change in electroacoustic response of the BAW resonator structure may be detected to indicate a presence and/or quantity of analyte bound to the functionalization material 38.

Having described fluidic devices 56, 58 of FIGS. 3 and 4 to provide context, fluidic devices including features configured to interact with fluid flowing within a fluidic passage to promote mixing between constituents of the fluid will now be described. In various embodiments, at least one of a wall structure, a cover structure, or a portion of a base structure bounding a fluidic passage includes multiple features (e.g., patterned features, such as multiple protrusions and/or recesses) configured to promote mixing of constituents of fluid within the passage.

Figure 5:
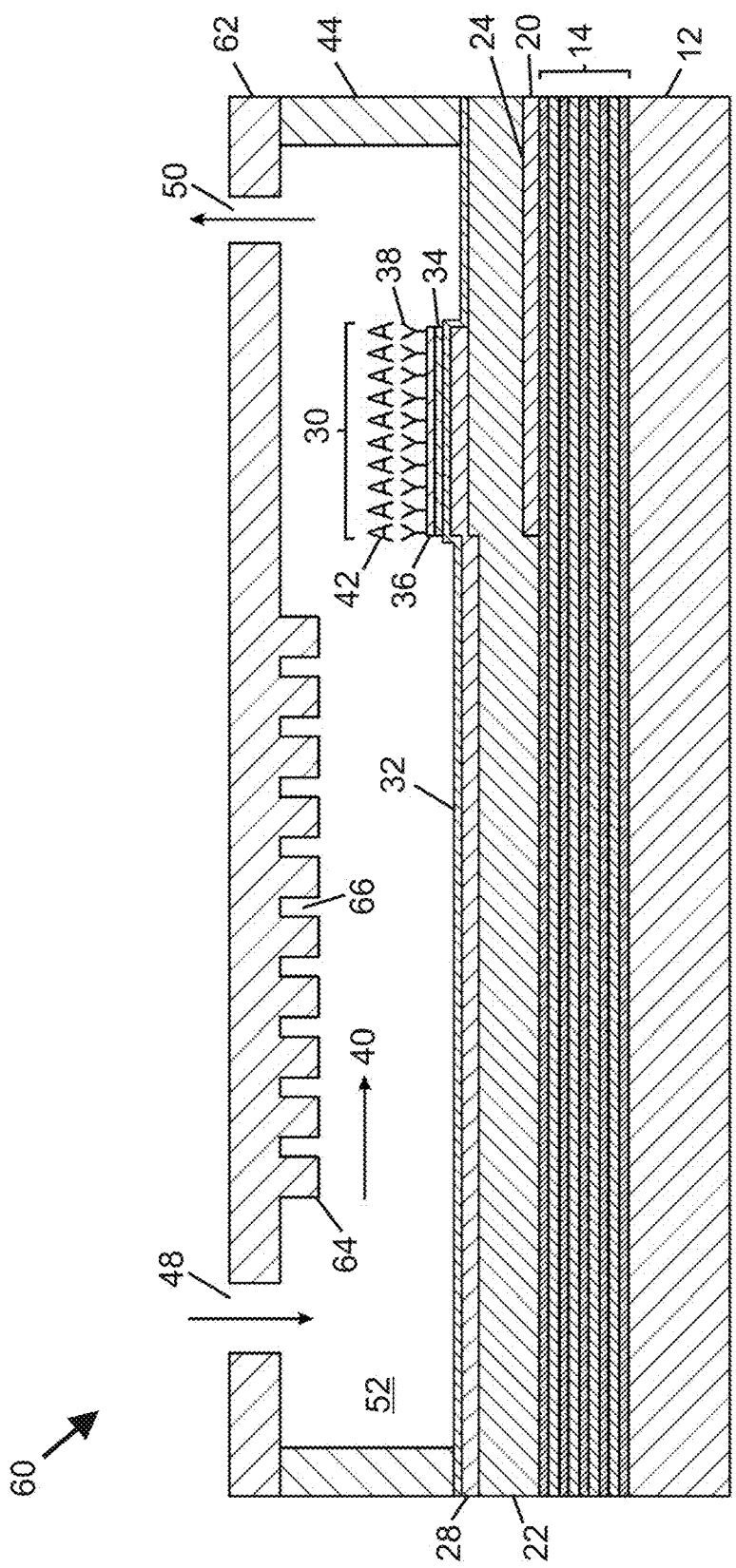
FIG. 5 is a schematic cross-sectional view of a portion of a fluidic device (e.g., a biochemical sensor device) including a fluidic passage bounded from below by a base structure include a BAW resonator structure, bounded laterally by a wall structure, and bounded from above by a cover structure defining inlet and outlet ports, with a SAM and functionalization material arranged over an active region, and with the cover structure including a first group of multiple features (e.g., downwardly extending protrusions or upwardly extending recesses) configured to interact with fluid flowing within the fluidic passage to promote mixing between constituents of the fluid.

FIG. 5 is a schematic cross-sectional view of a portion of a fluidic device (e.g., a biochemical sensor device) 60 including a fluidic passage 52 bounded from above by a cover structure 62 that includes a group of multiple mixing features (e.g., downwardly extending protrusions 64 and/or upwardly extending recesses 66) configured to interact with fluid 40 flowing within the fluidic passage 52 to promote mixing between constituents of the fluid 40. The fluidic passage 52 is further bounded from below by a BAW resonator structure and bounded laterally by a wall structure 44. The BAW resonator structure includes a substrate 12 overlaid with an acoustic reflector 14, and a bottom side electrode 20 arranged generally below a piezoelectric material 22. The bottom side electrode 20 is arranged along a portion of a lower surface 24 of the piezoelectric material 22. A top side electrode 28 extends over a portion of the piezoelectric material 22, wherein a portion of the piezoelectric material 22 arranged between the top side electrode 28 and the bottom side electrode 20 embodies the active region 30 of the BAW resonator structure. A hermeticity layer 32 is arranged over the top side electrode 28 and the piezoelectric material 22. An interface layer 34 and a SAM 36 are provided over a portion of the hermeticity layer 32 registered with the active region 30. The SAM 36 is overlaid with a layer of functionalization (e.g., specific binding) material 38 arranged to bind at least one analyte (e.g., analyte 42). The wall structure 44 includes walls that are laterally displaced from the active region 30 and that extend upward from the hermeticity layer 32 to define lateral boundaries of the fluidic passage 52 containing the active region 30. The cover structure 62 defines fluidic inlet and outlet ports 48, 50 and is provided over the wall structure 44 to provide an upper boundary for the fluidic passage 52. Multiple mixing features (e.g., downwardly extending protrusions 64 and/or upwardly extending recesses 66) defined in or on the cover structure 62 are arranged upstream of the active region 30 and are configured to promote mixing between constituents of the fluid 40 flowing with the fluidic passage 52, such as by causing fluid flowing within the fluidic passage 52 proximate to the cover structure 62 to depart from purely linear flow. Restated, fluid flowing proximate to the cover structure 62 may undergo a tortuous path, leading to localized fluid circulation that may tend to promote mixing of constituents of the fluid 40. The mixing features 64, 66 may be formed in or on the cover structure 62 by methods such as molding, selective etching (e.g., preceded by photolithographic patterning), three-dimensional printing, laser micromachining, selective deposition, and the like. More generally, the mixing features 64, 66 may be formed by a subtractive material removal process (e.g., etching, laser micromachining, etc.), and/or an additive manufacturing process (e.g., involving deposition of materials such as SU-8, photoresist, Parylene, epoxy, polymers, etc.).

In operation of the fluidic device 60, a fluid sample may be supplied through the fluidic inlet port 48 into the fluidic passage 52 to flow past the mixing features 64, 66 associated with the cover structure 62, and then flow over the active region 30 and through the fluidic outlet port 50 to exit the fluidic passage 52. Analyte 42 contained in the fluid 40 may bind with functionalization material 38 overlying the active region 30. When a bulk acoustic wave having a dominant shear component is induced in the active region 30 by supplying an electrical (e.g., alternating current) signal of a desired frequency to the bottom and top side electrodes 20, 28, a change in electroacoustic response (e.g., at least one of an amplitude-magnitude property, a frequency property, or a phase property, such as a shift in resonant frequency) of the BAW resonator structure may be detected to indicate a presence and/or quantity of analyte bound to the functionalization material 38.

Figure 6:
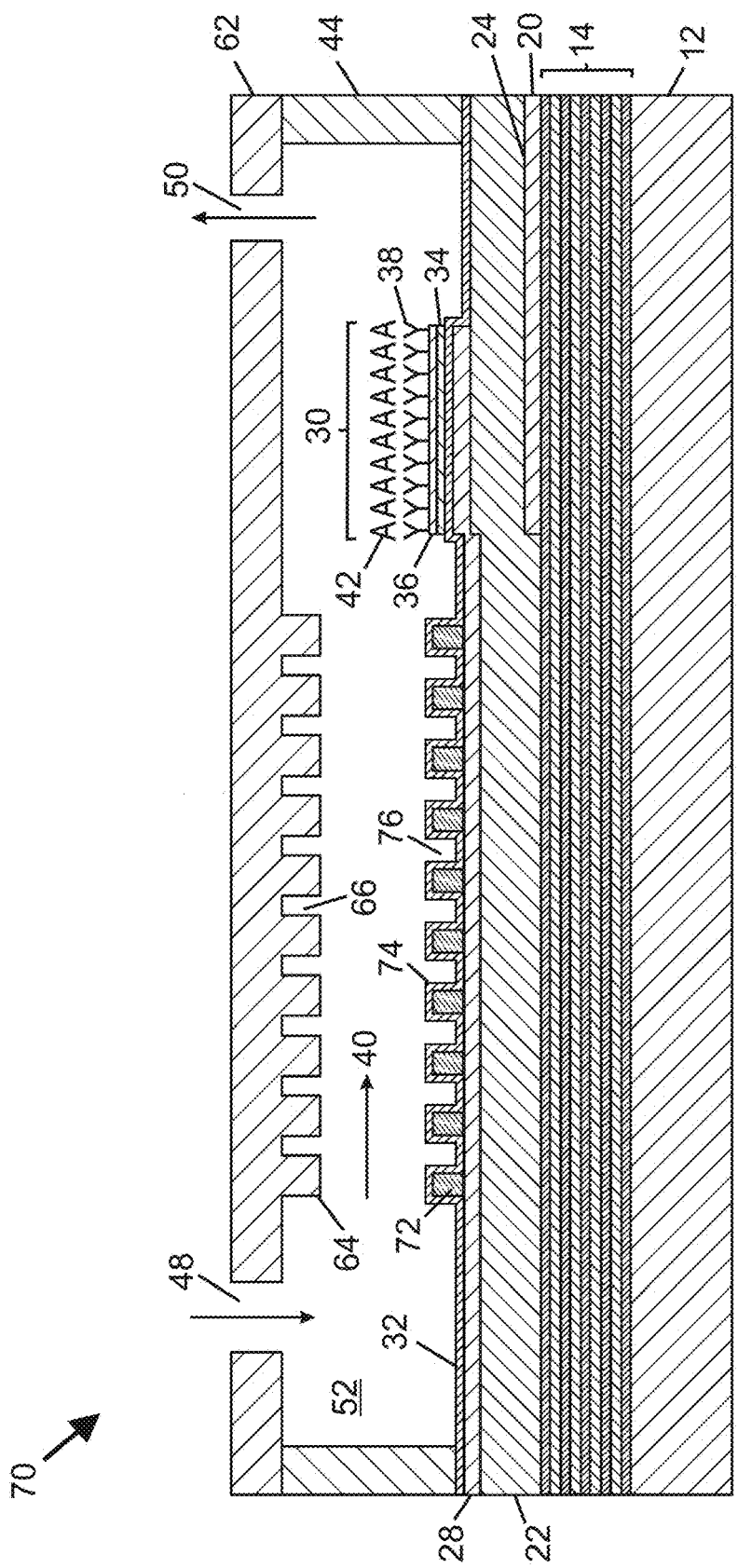
FIG. 6 is a schematic cross-sectional view of a portion of a fluidic device (e.g., a biochemical sensor device) that is substantially similar to the fluidic device of FIG. 5, except for modification of the base structure to include a second group of multiple features (e.g., upwardly extending protrusions and/or downwardly extending recesses) configured to interact with fluid flowing within the fluidic passage to promote mixing between constituents of the fluid.

In certain embodiments, multiple mixing features may be formed in or on a base structure of a fluidic device, with the base structure incorporating a BAW resonator structure. FIG. 6 illustrates at least a portion of a fluidic device (e.g., a biochemical sensor device) 70 that is similar to the fluidic device 60 of FIG. 5, except for modification of a base structure (bounding the fluidic passage 52 from below) to include another group of multiple features promote mixing between constituents of fluid 40 flowing within the fluidic passage 52. The fluidic passage 52 is bounded from below by a BAW resonator structure, bounded laterally by a wall structure 44, and bounded from above by a cover structure 62 that includes an additional group of multiple mixing features (e.g., downwardly extending protrusions 64 and/or upwardly extending recesses 66). The BAW resonator structure includes a substrate 12 overlaid with an acoustic reflector 14, and a bottom side electrode 20 arranged generally below a piezoelectric material 22. The bottom side electrode 20 is arranged along a portion of a lower surface 24 of the piezoelectric material 22. A top side electrode 28 extends over a portion of the piezoelectric material 22, wherein a portion of the piezoelectric material 22 arranged between the top side electrode 28 and the bottom side electrode 20 embodies an active region 30 of the BAW resonator structure. A hermeticity layer 32 is arranged over the top side electrode 28 and the piezoelectric material 22. An interface layer 34 and a SAM 36 are provided over a portion of the hermeticity layer 32 registered with the active region 30. The SAM 36 is overlaid with a layer of functionalization (e.g., specific binding) material 38 arranged to bind at least one analyte (e.g., analyte 42). The wall structure 44 includes walls that extend upward from the hermeticity layer 32 and that are covered with the cover structure 62, which defines fluidic inlet and outlet ports 48, 50. A first group of mixing features (e.g., downwardly extending protrusions 64 and/or upwardly extending recesses 66) is defined in or on the cover structure 62, and a second group of mixing features (e.g., upwardly extending protrusions 74 and/or downwardly extending recesses 76) is defined in or on a portion of the top side electrode 28 non-coincident with the active region 30. Both groups of mixing features 64, 66, 74, 76 are arranged between the fluidic inlet port 48 and the active region 30, to promote fluid mixing upstream of the active region 30. As shown in FIG. 6, the upwardly extending protrusions 74 may be formed by regions of deposited material 72, wherein the deposited material 72 as well as the top side electrode 28 (and any portions of the piezoelectric material 22 that would otherwise be uncovered) are covered with the hermeticity layer 32. Operation of the fluidic device 70 of FIG. 6 is substantially similar to operation of the fluidic device 60 described in connection with FIG. 5, except that presence of two groups of mixing features (e.g., mixing features 64, 66 associated with the cover structure 62, and mixing features 74, 76 associated with the base structure defining the BAW resonator structure) is expected to provide enhanced mixing of fluid 40 flowing through the fluidic passage 52 relative to the presence of a single group of mixing features as shown in FIG. 5.

Figure 7A:
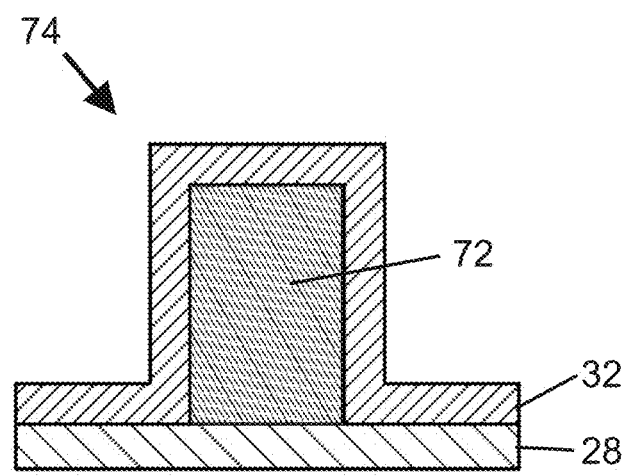
FIG. 7A is a magnified schematic cross-sectional view of a single protrusion (i.e., a mixing feature) arranged along a lower boundary of the fluidic passage of FIG. 6, including a deposited material (e.g., photoimageable material) extending upward from a surface of a top side electrode non-coincident with the active region, with the protrusion being overlaid with a hermeticity layer, according to one embodiment.

FIG. 7A is a magnified schematic cross-sectional view of a single protrusion 74 (i.e., a mixing feature) arranged along a lower boundary of the fluidic passage 52 of FIG. 6. The protrusion 74 includes a deposited material 72 arranged over a region of a top side electrode 28 non-coincident with an active region, with the deposited material 72 being overlaid with a hermeticity layer 32. Examples of materials that might be used for the deposited material 72 include, but are not limited to SU-8, photoresist, Parylene, epoxy, and polymers. In certain embodiments, a deposited material 72 may be applied over specified areas using an additive manufacturing process, and thereafter portions of the deposited material 72 may be removed using a subtractive process. In certain embodiments, the deposited material 72 comprises a photoimageable material to facilitate patterning.

Figure 7B:
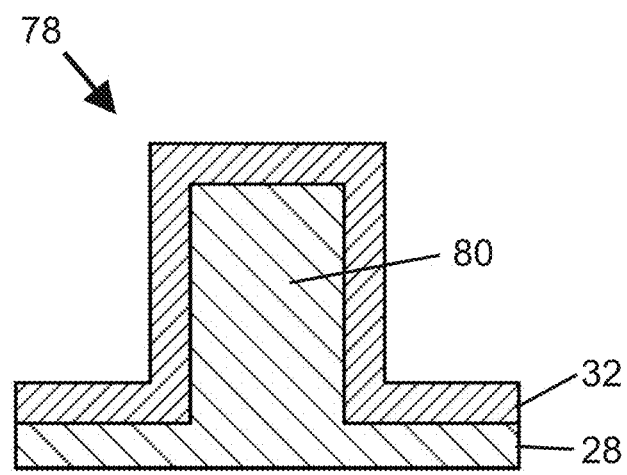
FIG. 7B is a magnified schematic cross-sectional view of a single protrusion of an alternative mixing feature including an upwardly extending portion of a top side electrode, with the protrusion being overlaid with a hermeticity layer, according to one embodiment.

FIG. 7B is a magnified schematic cross-sectional view of an alternative single protrusion 78 (i.e., a mixing feature) that could be arranged along a lower boundary of the fluidic passage 52 of FIG. 6. Instead of utilizing a deposited material, the protrusion 78 includes an upwardly extending portion 80 of a top side electrode 28 (non-coincident with an active region of a BAW resonator structure), with the upwardly extending portion 80 being overlaid with a hermeticity layer 32. In certain embodiments, the top side electrode 28 may be initially deposited with increased thickness, and regions of such material may be selectively removed (via any suitable subtractive material removal process) to form upwardly extending protrusions separated by troughs.

Although FIGS. 7A and 7B show protrusions formed by material deposition on a top side electrode or by selective removal of top side electrode material, in certain embodiments, protrusions may be formed by material deposition on a piezoelectric layer or by selective removal of piezoelectric material. Such protrusions may be overlaid with one or more additional layers, such as a hermeticity layer, a blocking layer, or the like.

Figure 8A:
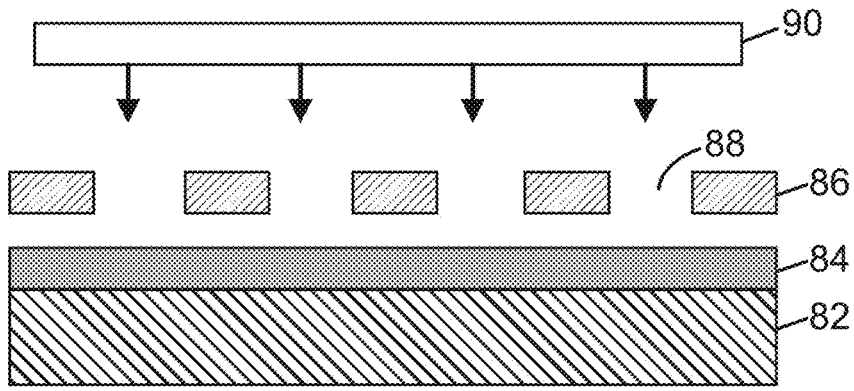
FIGS. 8A-8E provide schematic cross-sectional views of a portion of a top side electrode with recesses in various states of formation in an upper surface thereof.
Figure 8B:
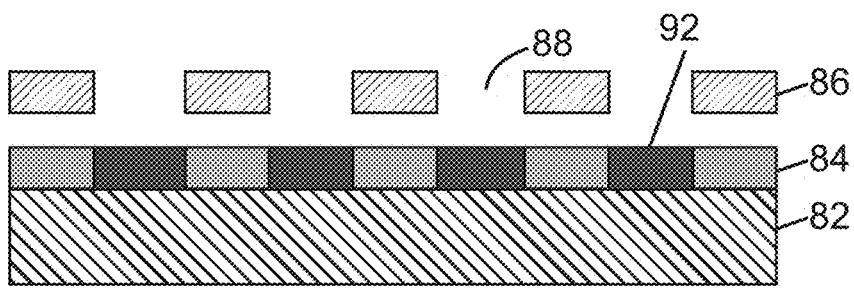
Figure 8C:
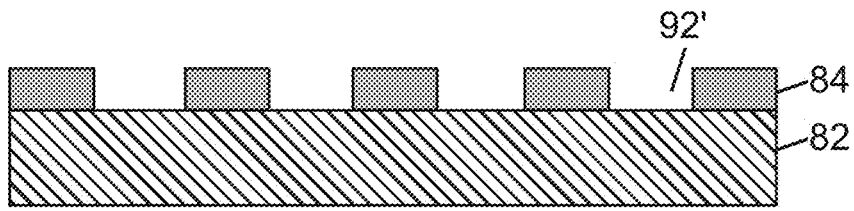
Figure 8D:
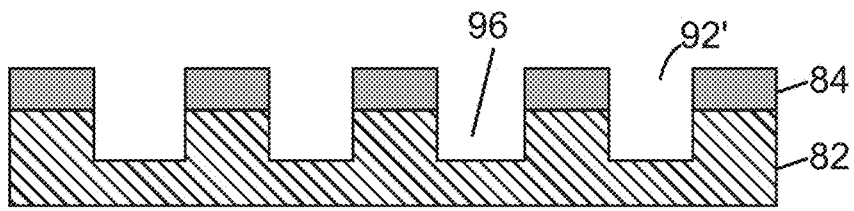
Figure 8E:
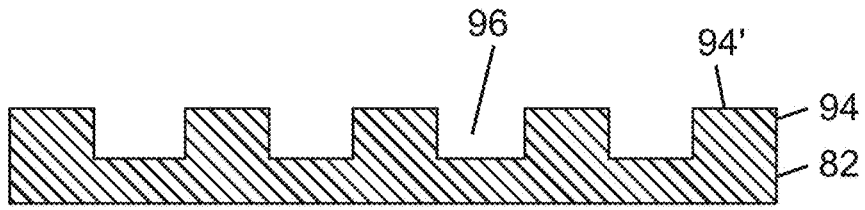

FIGS. 8A-8E provide schematic cross-sectional views of a portion of a piezoelectric material 82 with recesses in various states of formation in an upper surface thereof using a process such as photolithographic patterning followed by selective etching. FIG. 8A illustrates the piezoelectric material 82 overlaid with a layer of photoresist 84, with a photomask 86 defining mask windows 88 arranged between the layer of photoresist 84 and an electromagnetic (e.g., ultraviolet) radiation source 90. FIG. 8B illustrates the photomask 86, piezoelectric material 82, and layer of photoresist 84 following impingement of radiation through the mask windows 88 to form soluble regions 92 in the layer of photoresist 84. Such soluble regions 92 may be removed by application of a suitable developer chemical to yield a layer of photoresist 84 defining photoresist windows 92', as shown in FIG. 8C. Thereafter, a suitable etchant may be applied through the photoresist windows 92' to form grooves or recesses 96 in the piezoelectric material 82, as shown in FIG. 8D. Finally, the layer of photoresist 84 may be removed to yield a piezoelectric material 82 including an exposed upper surface 94' and grooves or recesses 96 that extend from the upper surface 94' into an interior of the piezoelectric material 82, as shown in FIG. 8E. The resulting grooves or recesses 96 are separated by elevated regions or protrusions 94, with the foregoing elements being useable as mixing features to promote mixing of fluid flowing within a fluidic passage bounded in part by these features. Although FIG. 8E shows the grooves or recesses 96 as extending through only a portion of a thickness of the piezoelectric material 82, in certain embodiments, one or more grooves or recesses 96 may extend through the entire thickness of the piezoelectric material 82.

In certain embodiments, multiple mixing features (e.g., protrusions and/or recesses) may be formed in or on a wall structure of a fluidic device, with the wall structure forming a lateral boundary of a fluidic passage. In certain embodiments, such mixing features may be formed by processes such as micromolding, laser patterning, three dimensional printing, cutting through stencil layers, or other suitable processes known in the art.

Figure 9A:
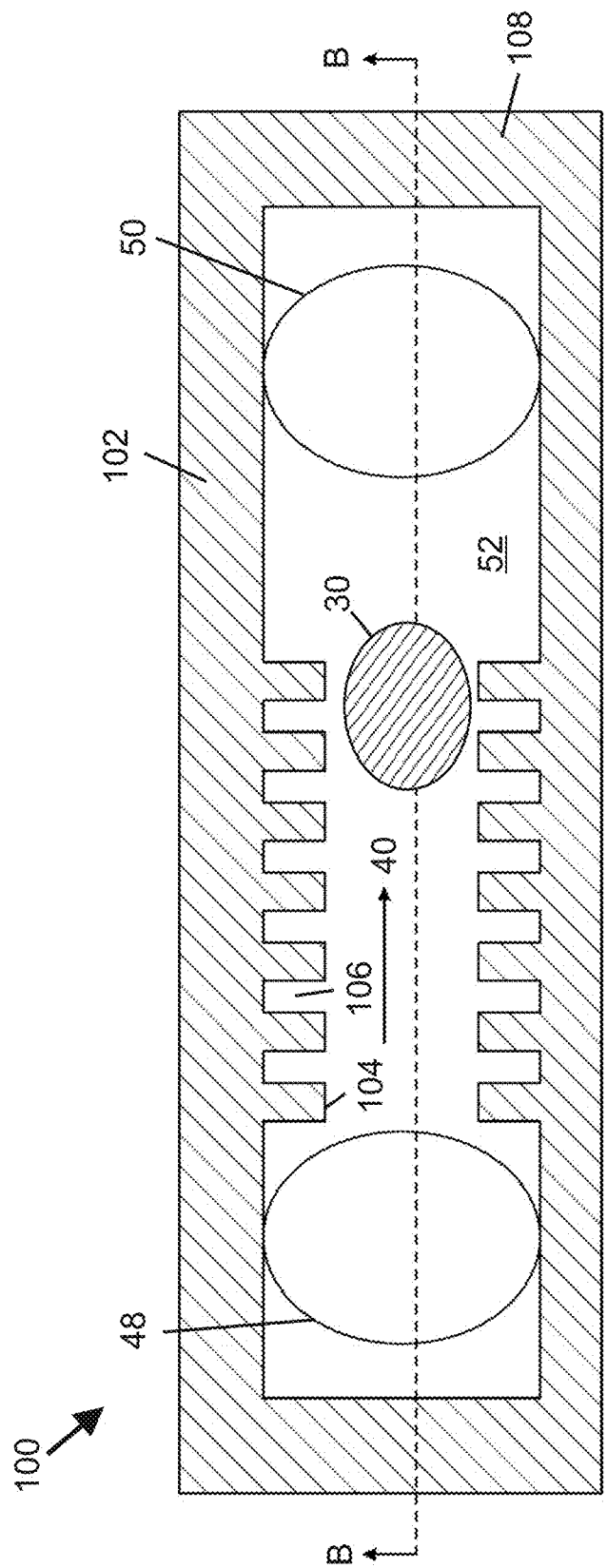
FIG. 9A is a schematic top plan view of at least a portion of a fluidic device (e.g., a biochemical sensor device) including a fluidic passage bounded from below by a base structure include a BAW resonator structure, bounded laterally by a wall structure, and bounded from above by a cover structure defining a fluidic inlet port and a fluidic outlet port, and with the wall structure including multiple features (e.g., medially extending protrusions or outwardly extending recesses) configured to interact with fluid flowing within the fluidic passage to promote mixing between constituents of the fluid.

FIG. 9A is a schematic top plan view of at least a portion of a fluidic device 100 (e.g., a biochemical sensor device) including a fluidic passage 52 bounded laterally by a wall structure 108 that includes end walls 102 and multiple mixing features (e.g., medially extending protrusions 104 or outwardly extending recesses 106) configured to interact with fluid 40 flowing within the fluidic passage 52 to promote mixing between constituents of the fluid 40. The fluidic passage 52 is bounded from below by a base structure including a BAW resonator structure, and is bounded from above by a cover structure defining a fluidic inlet port 48 and a fluidic outlet port 50 with an active region 30 of the BAW resonator structure arranged therebetween. A majority of the mixing features 104, 106 are arranged between the fluidic inlet port 48 and the active region 30.

Figure 9B:
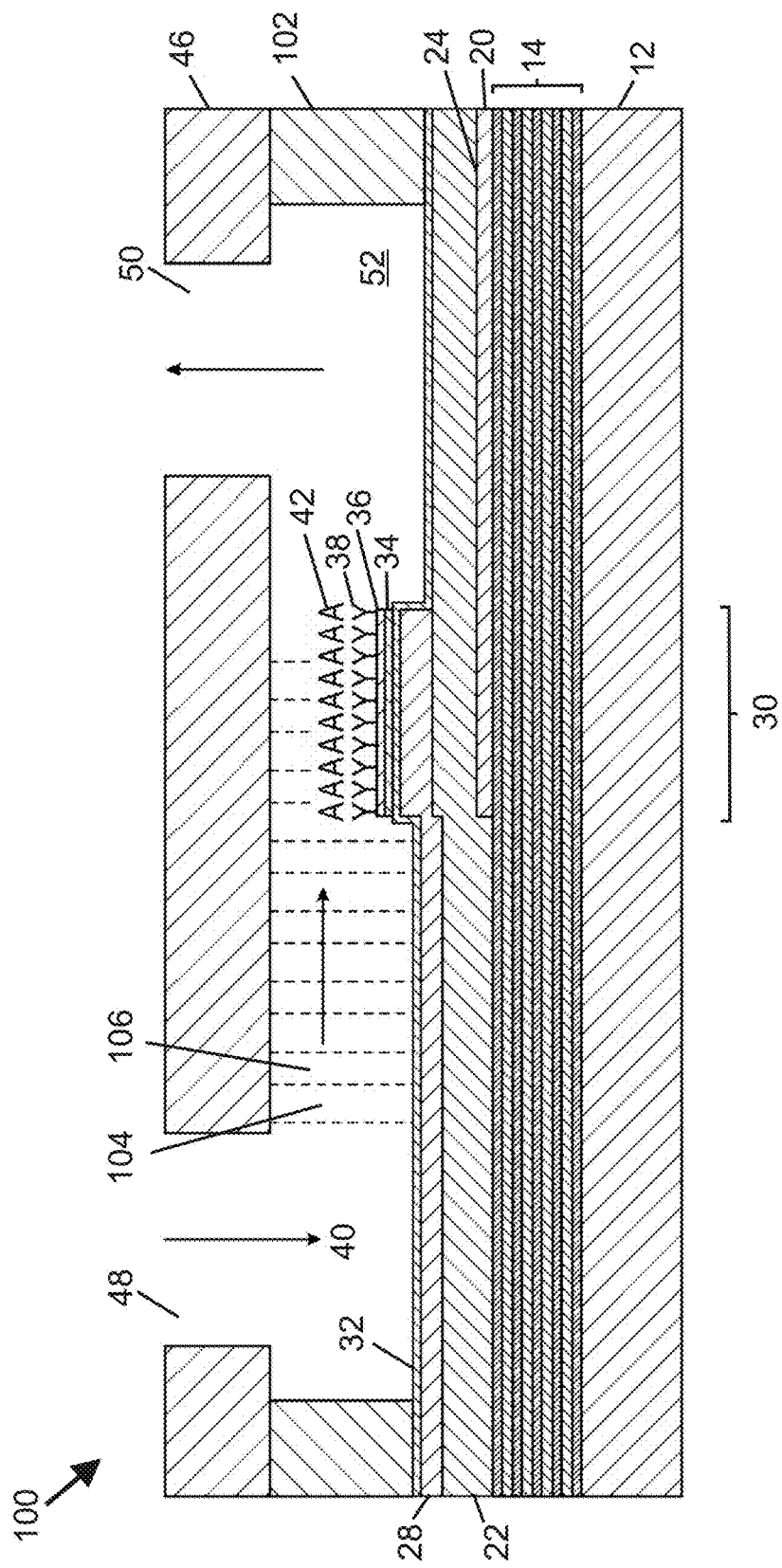
FIG. 9B is a schematic cross-sectional view of the at least a portion of a fluidic device of FIG. 9A taken along section lines B-B shown in FIG. 9A.

FIG. 9B is a schematic cross-sectional view of the at least a portion of the fluidic device 100 of FIG. 9A taken along section lines B-B shown in FIG. 9A. As shown, the fluidic passage 52 is bounded from above by a cover structure in the form of cover or cap layer 46, and from below by a base structure including a BAW resonator structure. The BAW resonator structure includes a substrate 12 overlaid with an acoustic reflector 14, and a bottom side electrode 20 arranged generally below a piezoelectric material 22. The bottom side electrode 20 is arranged along a portion of a lower surface 24 of the piezoelectric material 22. A top side electrode 28 extends over a portion of the piezoelectric material 22, wherein a portion of the piezoelectric material 22 arranged between the top side electrode 28 and the bottom side electrode 20 embodies the active region 30 of the BAW resonator structure. A hermeticity layer 32 is arranged over the top electrode 28 and the piezoelectric material 22. An interface layer 34 and a SAM 36 are provided over a portion of the hermeticity layer 32 registered with the active region 30. The SAM 36 is overlaid with a layer of functionalization (e.g., specific binding) material 38 arranged to bind at least one analyte (e.g., analyte 42). End walls 102 of the wall structure 108 (shown in FIG. 9A) are laterally displaced from the active region 30 and extend upward from the hermeticity layer 32 to define lateral boundaries of the fluidic passage 52 containing the active region 30. The cover or cap layer 46 defines fluidic inlet and outlet ports 48, 50 and is provided over end walls 102 of the wall structure to provide an upper boundary for the fluidic passage 52. Medially extending protrusions 104 or outwardly extending recesses 106 embodying mixing features are illustrated in vertical broken lines in FIG. 9B, spanning between the cover or cap layer 46 and the base structure incorporating the BAW resonator structure, with a majority of such mixing features being arranged generally between the fluidic inlet port 48 and the active region 30. The medially extending protrusions 104 or outwardly extending recesses 106 embodying mixing features are configured to promote mixing between constituents of fluid 40 flowing with the fluidic passage 52, such as by causing fluid flowing within the fluidic passage 52 proximate to side walls of the wall structure 108 to undergo a tortuous path, leading to localized fluid circulation that may tend to promote mixing of constituents of the fluid 40.

In operation of the fluidic device 100, a fluid sample may be supplied through the fluidic inlet port 48 into the fluidic passage 52 to flow past the mixing features 104, 106 associated with the wall structure 108, and then flow over the active region 30 and through the fluidic outlet port 50 to exit the fluidic passage 52. Analyte 42 contained in the fluid 40 may bind with functionalization material 38 overlying the active region 30. When a bulk acoustic wave having a dominant shear component is induced in the active region 30 by supplying an electrical (e.g., alternating current) signal of a desired frequency to the bottom and top side electrodes 20, 28, a change in electroacoustic response (e.g., at least one of an amplitude-magnitude property, a frequency property, or a phase property, such as a shift in resonant frequency) of the BAW resonator structure may be detected to indicate a presence and/or quantity of analyte bound to the functionalization material 38.

It is to be appreciated that mixing features embodying protrusions and/or recesses may be provided in various numbers, shapes, and configurations. Some illustrative examples of mixing features are shown in FIGS. 10-12.

Figure 10:
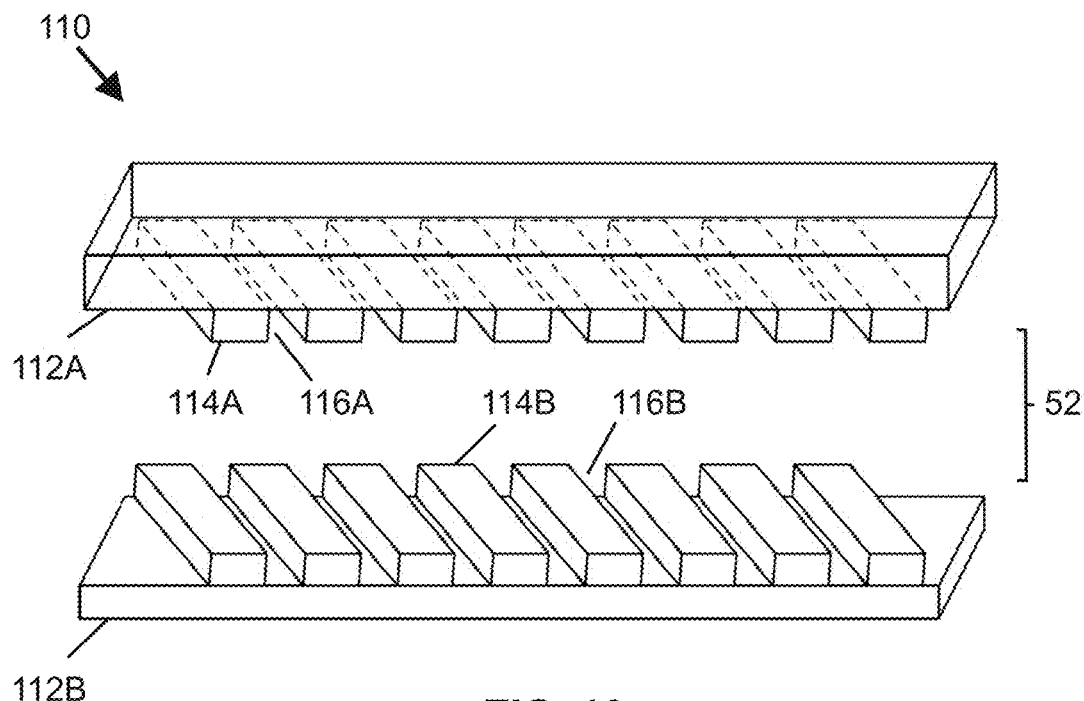
FIG. 10 is a schematic perspective view of two opposing structures configured to bound a fluidic passage and including protrusions embodied in diagonally extending parallel beams configured to interact with fluid flowing within the fluidic passage to promote mixing between constituents of the fluid, according to one embodiment.

FIG. 10 illustrates a portion of a fluidic device 110 including two opposing structures 112A, 112B configured to bound a fluidic passage 52, with the opposing structures 112A, 112B including protrusions 114A, 114B embodied in diagonally extending parallel beams separated by recesses 116A, 116B. Such protrusions 114A, 114B and recesses 116A, 116B are configured to interact with fluid flowing within the fluidic passage 52 to promote mixing between constituents of the fluid, according to one embodiment.

Figure 11:
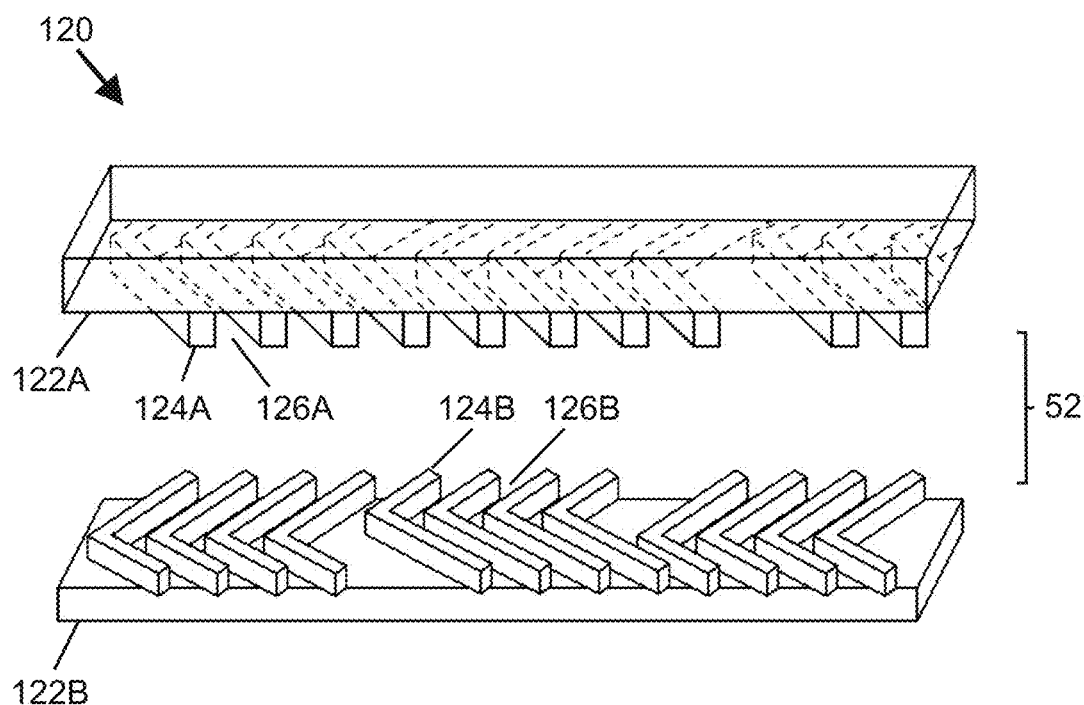
FIG. 11 is a schematic perspective view of two opposing structures configured to bound a fluidic passage and including protrusions embodied in a staggered herringbone pattern configured to interact with fluid flowing within the fluidic passage to promote mixing between constituents of the fluid, according to one embodiment.

FIG. 11 illustrates a portion of a fluidic device 120 including two opposing structures 122A, 122B configured to bound a fluidic passage 52, with the opposing structures 122A, 122B including protrusions 124A, 124B embodied in a staggered herringbone pattern and separated by recesses 126A, 126B. Such protrusions 124A, 124B and recesses 126A, 126B are configured to interact with fluid flowing within the fluidic passage 52 to promote mixing between constituents of the fluid, according to one embodiment.

Figure 12:
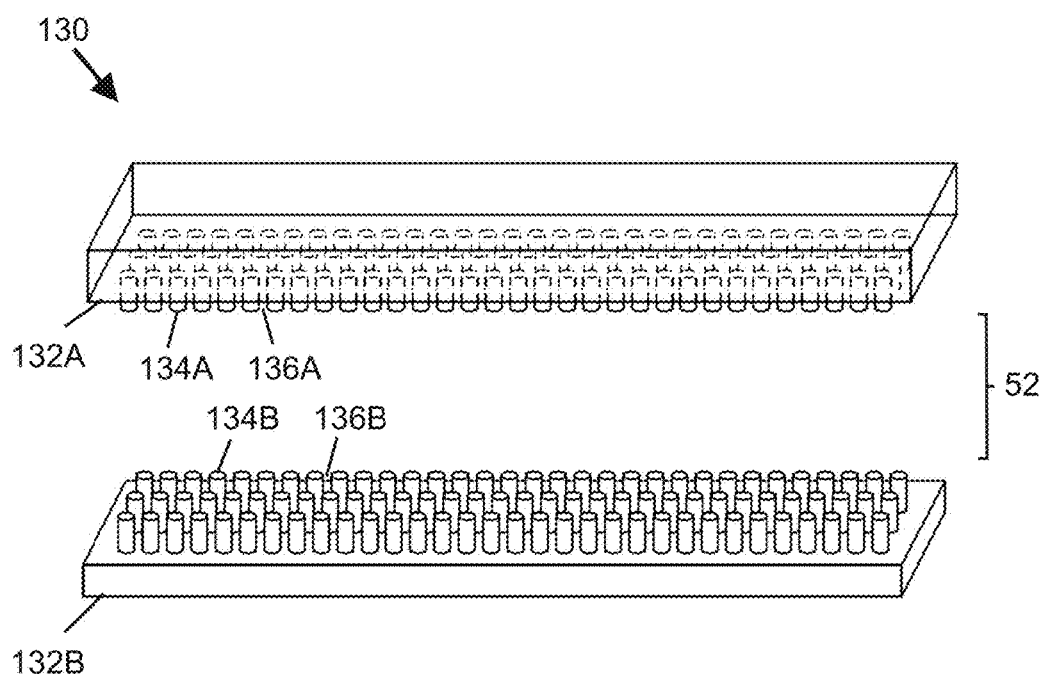
FIG. 12 is a schematic perspective view of two opposing structures configured to bound a fluidic passage and including protrusions embodied in an array of cylindrical pillars configured to interact with fluid flowing within the fluidic passage to promote mixing between constituents of the fluid, according to one embodiment.

FIG. 12 illustrates a portion of a fluidic device 130 including two opposing structures 132A, 132B configured to bound a fluidic passage 52, with the opposing structures 132A, 132B including protrusions 134A, 134B embodied in arrays of cylindrical pillars separated by recesses 136A, 136B. Such protrusions 134A, 134B and recesses 136A, 136B are configured to interact with fluid flowing within the fluidic passage 52 to promote mixing between constituents of the fluid, according to one embodiment.

Although various embodiments disclosed herein illustrate mixing features defined by a base structure, a wall structure, or a cover structure, in certain embodiments, mixing features may be defined by any two or all three of the foregoing structures. Additionally, mixing features of multiple types, sizes, and/or shapes may be provided on any one, any two, or all three of a base structure, a wall structure, and/or a cover structure.

FIG. 13A is a schematic cross-sectional view of a film bulk acoustic wave resonator (FBAR) structure 150 including an active region 30, wherein at least portions of the active region 30 are subject to being overlaid with an interface layer and a self-assembled monolayer (SAM) suitable for receiving a functionalization (e.g., specific binding or non-specific binding) material, according to one embodiment. The FBAR structure 150 includes a substrate 152 (e.g., silicon or another semiconductor material) defining a cavity 154 optionally covered by a support layer 156 (e.g., silicon dioxide). A bottom side electrode 20 is arranged over a portion of the support layer 156, a piezoelectric material 22, preferably embodying inclined c-axis hexagonal crystal structure piezoelectric material (e.g., AlN or ZnO), is arranged over the bottom side electrode 20 and the support layer 156, and a top side electrode 28 is arranged over at least a portion of a top surface of the piezoelectric material 22. A portion of the piezoelectric material 22 arranged between the top side electrode 28 and the bottom side electrode 20 embodies the active region 30 of the FBAR structure 150. The active region 30 is arranged over and registered with the cavity 154 disposed below the support layer 156. The cavity 154 serves to confine acoustic waves induced in the active region 30 by preventing dissipation of acoustic energy into the substrate 152, since acoustic waves do not efficiently propagate across the cavity 154. In this respect, the cavity 154 provides an alternative to the acoustic reflector 14 illustrated in FIGS. 1, 3-6, and 9B. Although the cavity 154 shown in FIG. 13A is bounded from below by a thinned portion of the substrate 152, in alternative embodiments at least a portion of the cavity 154 may extend through an entire thickness of the substrate 152. Steps for forming the FBAR structure 150 may include defining the cavity 154 in the substrate 152, filling the cavity 154 with a sacrificial material (not shown) optionally followed by planarization of the sacrificial material, depositing the support layer 156 over the substrate 152 and the sacrificial material, removing the sacrificial material (e.g., by flowing an etchant through vertical openings defined in the substrate 152 or the support layer 156, or lateral edges of the substrate 152), depositing the bottom side electrode 20 over the support layer 156, growing (e.g., via sputtering or other appropriate methods) the piezoelectric material 22, and depositing the top side electrode 28. In certain embodiments, the top side electrode 28, piezoelectric material 22, and the bottom side electrode 20 in combination may be self-supporting, and the support layer 156 may be omitted and/or removed by etching in the vicinity of the active region 30.

FIG. 13B is a schematic cross-sectional view of the FBAR structure 150 according to FIG. 13A, following addition of a hermeticity layer 32, an interface layer 34, a self-assembled monolayer 36, and functionalization material 38 (e.g., specific binding material). The hermeticity layer 32 is arranged over the entire piezoelectric material 22 (as well as the top side electrode 28), whereas the functionalization material 38, the SAM 36, and the interface layer 34 are arranged solely over the active region 30. As shown in FIG. 13B, analyte 42 is bound to the functionalization material 38, such as may occur following exposure of the functionalization material 38 to a medium (e.g., liquid or other fluid) containing the analyte 42, optionally as part of a microfluidic device.

As will be recognized by one skilled in the art upon review of the present disclosure, in certain embodiments, the FBAR structure 150 of FIGS. 13A and 13B may be substituted for the solidly mounted BAW resonator structures disclosed previously herein. In certain embodiments, the FBAR structure 150 of FIG. 13B may be incorporated in a fluidic device (e.g., microfluidic device) including multiple features (e.g., protrusions and/or recesses) defined in or on one or more of a base structure, a wall structure, or a cover structure, in order to interact with fluid flowing within a fluidic passage to promote mixing between constituents of the fluid.

Figure 14:
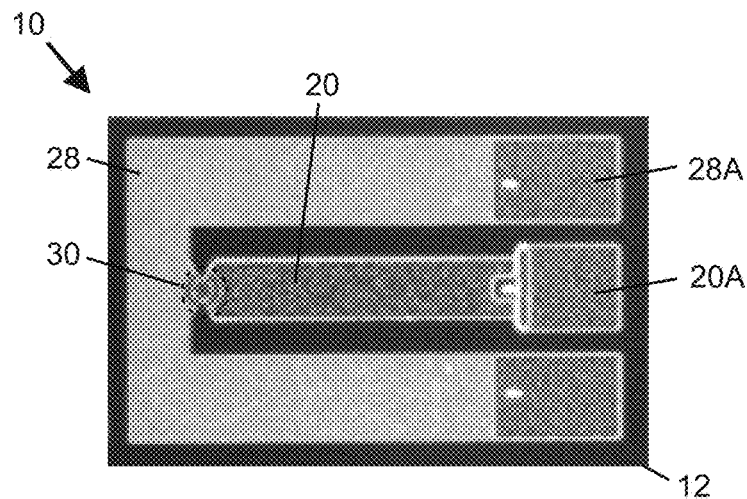
FIG. 14 is a top plan view photograph of a bulk acoustic wave MEMS resonator device suitable for receiving a hermeticity layer, an interface layer, a self-assembled monolayer, and functionalization (e.g. specific binding) material as disclosed herein.

FIG. 14 is a top plan view photograph of a bulk acoustic wave MEMS resonator device 10 (consistent with the portion of the resonator device 10 illustrated in FIG. 1) suitable for receiving a hermeticity layer, an interface layer, a self-assembled monolayer, and/or functionalization (e.g., specific binding) material as disclosed herein, wherein the MEMS resonator device 10 may serve as a base structure of a fluidic device as disclosed herein. The MEMS resonator device 10 includes a piezoelectric material (not shown) arranged over a substrate 12, a bottom side electrode 20 arranged under a portion of the piezoelectric material, and a top side electrode 28 arranged over a portion of the piezoelectric material, including an active region 30 in which the piezoelectric material is arranged between overlapping portions of the top side electrode 28 and the bottom side electrode 20. Externally accessible contacts 20A, 28A are in electrical communication with the bottom side electrode 20 and the top side electrode 28, respectively. After portions of the resonator device 10 are overlaid with an interface layer, a self-assembled monolayer, and functionalization (e.g., specific binding) material as disclosed herein, the resonator device 10 may be used as a sensor and/or incorporated into a microfluidic device. If desired, multiple resonator devices 10 may be provided in an array on a single substrate 12.

Figure 15:
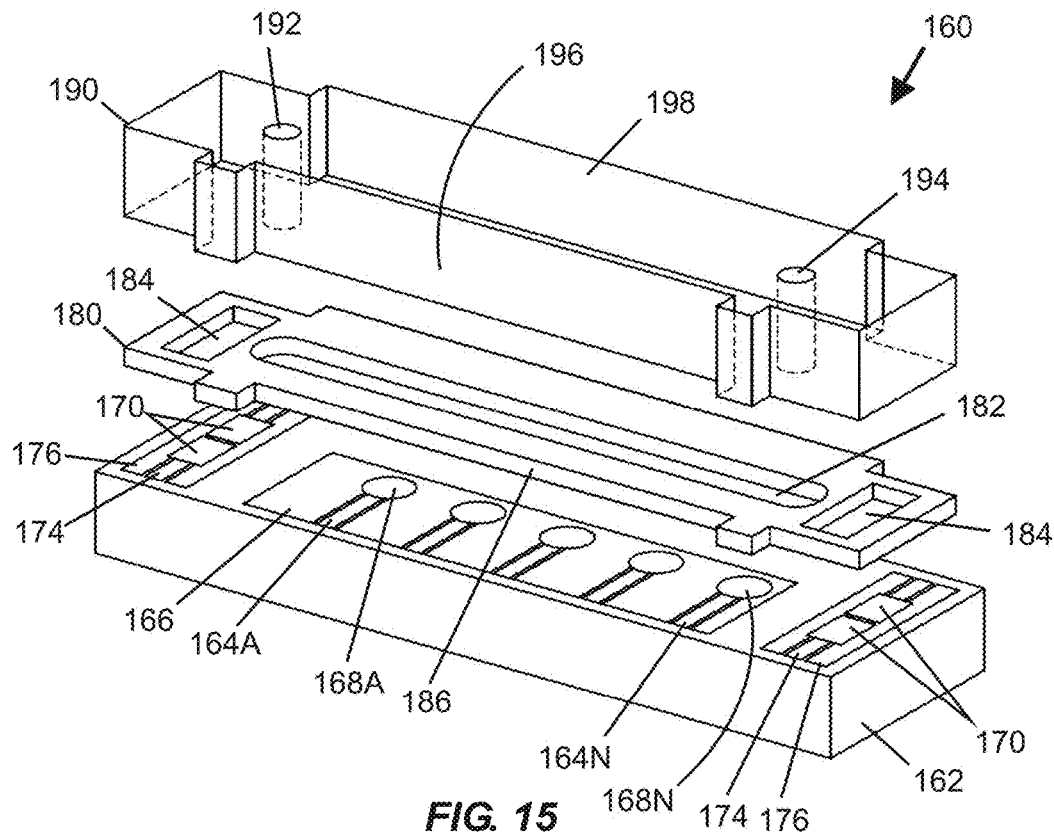
FIG. 15 is a perspective assembly view of a microfluidic device incorporating a base structure including multiple bulk acoustic wave MEMS resonator devices as disclosed herein, an intermediate wall structure layer defining lateral boundaries of a microfluidic channel containing active regions of the MEMS resonator devices, and a cover structure layer defining an upper boundary of the microfluidic channel.

FIG. 15 is a perspective assembly view of a microfluidic device 160 incorporating a substrate 162 with multiple bulk acoustic wave MEMS resonator devices (forming a base structure), an intermediate wall structure layer 180 defining a central microfluidic channel 182 registered with active regions 168A-168N of the MEMS resonator devices, and a cover structure layer 190 arranged to cover the wall structure layer 180. Top central portions of the substrate 162, which includes an acoustic reflector (not shown) and a piezoelectric material (not shown), include a top side electrode 166 and bottom side electrodes 164A-164N. Regions in which the foregoing electrodes overlap one another and sandwich the piezoelectric material embody active regions 168A-168N. Any suitable number of active regions 168A-168N may be provided and fluidically arranged in series or parallel, although five active regions are illustrated in FIG. 15. Top peripheral (or top end) portions of the substrate 162 further include reference top side electrodes 176 and reference bottom side electrodes 174 in communication with reference overlap regions 170. Such reference overlap regions 170 are not exposed to fluid, and are present to provide a basis for comparing signals obtained from the active regions 168A-168N exposed to fluid within the central microfluidic channel 182. The substrate 162 is overlaid with the wall structure layer 180, wherein the central microfluidic channel 182 is intended to receive fluid, and defines peripheral chambers 184 arranged to overlie the reference overlap regions 170 in a sealed fashion. The wall structure layer 180 may be formed of any suitable material such as SU-8 negative epoxy resist, other photoresist material, or laser-cut "stencil" layers of thin polymeric materials optionally including one or more self-adhesive surfaces (e.g., adhesive tape), etc. The wall structure layer 180 further includes a lateral inset region 186 that enables lateral portions of the top side electrode 166 and bottom side electrodes 164A-164N to be accessed upon assembly of the microfluidic device 160. The cover structure layer 190 includes a lateral inset region 196 registered with the lateral inset region 186 of the wall structure layer 180, and includes microfluidic ports 192, 194 accessible along a top surface 198 of the cover structure layer 190 and registered with end portions of the central microfluidic channel 182 defined in the wall structure layer 180 to permit fluid (e.g., liquid) to be supplied to the central microfluidic channel 182 over the active regions 168A-168N. Preferably, at least the electrodes 164A-164N, 166 are overlaid with a hermeticity layer, an interface layer, a self-assembled monolayer, and functionalization (e.g., specific binding) material as disclosed herein. In certain embodiments, a driving circuits may be configured to apply alternating current to the electrodes 164A-164N, 166 to cause the piezoelectric material to selectively exhibit a dominant shear response. Although not shown, it is to be appreciated that multiple protrusions and/or recesses may be defined in or on one or more of the following: the base structure (extending upward from piezoelectric material and/or electrodes formed over the substrate 162), the wall structure layer 180, or the cover structure layer 190. Microfluidic devices according to other configurations may be provided, as will be recognized by those skilled in the art upon review of the present disclosure.

Technical benefits obtainable with various embodiments of the present disclosure may include one or more of the following: enhanced rate of analyte binding to functionalization material overlying an active region of a bulk acoustic wave resonator structure, thereby reducing the time required to complete measurement of a particular sample, and/or enhanced mixing of analyte-containing fluids in fluidic devices incorporating bulk acoustic wave resonator structures, including devices suitable for biosensing or biochemical sensing applications.

Those skilled in the art will recognize improvements and modifications to the preferred embodiments of the present disclosure. All such improvements and modifications are considered within the scope of the concepts disclosed herein and the claims that follow.

What is claimed is:

1. A fluidic device comprising:
a base structure comprising: (i) a substrate; (ii) at least one bulk acoustic wave resonator structure supported by the substrate, the at least one bulk acoustic wave resonator structure including a piezoelectric material, a top side electrode arranged over a portion of the piezoelectric material, and a bottom side electrode arranged below at least a portion of the piezoelectric material, wherein a portion of the piezoelectric material is arranged between the top side electrode and the bottom side electrode to form an active region; and (iii) at least one functionalization material arranged over at least a portion of the active region;
a wall structure arranged over at least a portion of the base structure and defining lateral boundaries of a fluidic passage containing the active region and being configured to receive a fluid comprising multiple constituents; and
a cover structure arranged over the wall structure and defining an upper boundary of the fluidic passage;
wherein the base structure defines a lower boundary of the fluidic passage; and
wherein one or more of the wall structure, the cover structure, or a portion of the base structure non-coincident with the active region comprises a plurality of features configured to interact with fluid flowing within the fluidic passage to promote mixing between constituents of the fluid.

2. The fluidic device of claim 1, wherein the plurality of features is defined in or on the wall structure.

3. The fluidic device of claim 1, wherein the plurality of features is defined in or on the cover structure.

4. The fluidic device of claim 1, wherein the plurality of features is defined in or on a portion of the base structure non-coincident with the active region.

5. The fluidic device of claim 1, wherein the plurality of features comprises a plurality of recesses or a plurality of protrusions.

6. The fluidic device of claim 1, wherein the wall structure and the cover structure are embodied in a monolithic body structure.

7. The fluidic device of claim 1, wherein the wall structure and the base structure are embodied in a monolithic body structure.

8. The fluidic device of claim 1, wherein the cover structure comprises a cover layer, the wall structure comprises at least one wall layer, and the at least one wall layer is arranged between the base structure and the cover layer.

9. The fluidic device of claim 1, wherein the at least one bulk acoustic wave resonator structure comprises a plurality of bulk acoustic wave resonator structures.

10. The fluidic device of claim 1, wherein the base structure further comprises at least one acoustic reflector element arranged between the substrate and the at least one bulk acoustic wave resonator structure.

11. The fluidic device of claim 1, wherein the substrate defines a recess arranged below the active region.

12. The fluidic device of claim 1, wherein the piezoelectric material comprises a c-axis having an orientation distribution that is predominantly non-parallel to normal of a face of the substrate.

13. The fluidic device of claim 1, wherein the at least one functionalization material comprises a specific binding material or a non-specific binding material.

14. The fluidic device of claim 1, further comprising a self-assembled monolayer arranged between the at least one functionalization material and the top side electrode.

15. The fluidic device of claim 14, further comprising an interface layer arranged between the self-assembled monolayer and the top side electrode.

16. The fluidic device of claim 15, further comprising a hermeticity layer arranged between the interface layer and the top side electrode.

17. A method for biological or chemical sensing, the method comprising:
supplying a fluid containing an analyte into the fluidic passage of the fluidic device according to claim 1, wherein said supplying is configured to cause at least some of the analyte to bind to the at least one functionalization material;

inducing a bulk acoustic wave in the active region; and sensing a change in at least one of an amplitude-magnitude property, a frequency property, or a phase property of the at least one bulk acoustic wave resonator structure to indicate at least one of presence or quantity of target species bound to the at least one functionalization material.

18. A method for fabricating a fluidic device, the method comprising:

forming a base structure including at least one bulk acoustic wave resonator structure supported by a substrate, wherein the at least one bulk acoustic wave resonator structure includes a piezoelectric material, a top side electrode is arranged over a portion of the piezoelectric material, a bottom side electrode is arranged below at least a portion of the piezoelectric material, and a portion of the piezoelectric material is arranged between the top side electrode and the bottom side electrode to form an active region;

forming a wall structure over at least a portion of the base structure and defining lateral boundaries of a fluidic passage containing the active region and being configured to receive a fluid comprising multiple constituents;

forming a cover structure arranged over the wall structure and defining an upper boundary of the fluidic passage, wherein a lower boundary of the fluidic passage is defined by the base structure; and depositing at least one functionalization material over the active region;

wherein at least one of (i) formation of the base structure, (ii) formation of the wall structure, or (iii) formation of the cover structure comprises forming a plurality of features configured to interact with fluid flowing within the fluidic passage to promote mixing between constituents of the fluid, and the plurality of features comprises at least one of a plurality of recesses or a plurality of protrusions.

19. The method of claim 18, wherein the forming of a plurality of features configured to interact with fluid flowing within the fluidic passage comprises removing material of one or more of the wall structure, the cover structure, or the base structure via a subtractive material removal process.

20. The method of claim 18, wherein the forming of a plurality of features configured to interact with fluid flowing within the fluidic passage comprises adding material to one or more of the wall structure, the cover structure, or the base structure via an additive manufacturing process.

* * * * *